United States Patent
Ochs et al.

(10) Patent No.: US 8,398,555 B2
(45) Date of Patent: Mar. 19, 2013

(54) SYSTEM AND METHOD FOR DETECTING VENTILATORY INSTABILITY

(75) Inventors: James Ochs, Seattle, WA (US); Keith Batchelder, New York, NY (US); Yu-Jung Pinto, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1107 days.

(21) Appl. No.: 12/208,087

(22) Filed: Sep. 10, 2008

(65) Prior Publication Data

US 2010/0063366 A1 Mar. 11, 2010

(51) Int. Cl.
*A61B 5/08* (2006.01)

(52) U.S. Cl. ........................................ 600/484

(58) Field of Classification Search ................. None
See application file for complete search history.

(56) References Cited

U.S. PATENT DOCUMENTS

| | | |
|---|---|---|
| 4,106,503 A | 8/1978 | Rosenthal et al. |
| 4,365,636 A | 12/1982 | Barker |
| 4,523,279 A | 6/1985 | Sperinde |
| 4,630,614 A | 12/1986 | Atlas |
| 4,651,746 A | 3/1987 | Wall |
| 4,738,266 A | 4/1988 | Thatcher |
| 4,757,824 A | 7/1988 | Chaumet |
| 4,765,340 A | 8/1988 | Sakai et al. |
| 4,802,485 A | 2/1989 | Bowers et al. |
| 4,869,253 A | 9/1989 | Craig |
| 5,123,420 A | 6/1992 | Paret |
| 5,134,995 A | 8/1992 | Gruenke et al. |
| 5,199,424 A | 4/1993 | Sullivan |
| 5,206,807 A | 4/1993 | Hatke |
| 5,218,962 A | 6/1993 | Mannheimer et al. |
| 5,233,983 A | 8/1993 | Markowitz |
| 5,273,036 A | 12/1993 | Kronberg et al. |
| 5,275,159 A | 1/1994 | Griebel |
| 5,303,699 A | 4/1994 | Bonassa et al. |
| 5,318,597 A | 6/1994 | Hauck et al. |
| 5,329,931 A | 7/1994 | Clauson et al. |
| 5,335,654 A | 8/1994 | Rapoport |
| 5,353,788 A | 10/1994 | Miles |
| 5,368,026 A | 11/1994 | Swedlow et al. |
| 5,385,144 A | 1/1995 | Yamanishi et al. |

(Continued)

FOREIGN PATENT DOCUMENTS

| | | |
|---|---|---|
| DE | 9 200 422.9 | 7/1992 |
| EP | 0459284 B1 | 1/1995 |

(Continued)

OTHER PUBLICATIONS

Kiely et al., Comparison of a limited computerized diagnostic system (ResCare Autoset) with polysomnography in the diagnosis of obstructive sleep apnoea syndrome, 1996, Eur Respir J, 9: pp. 2360-2364.*

(Continued)

*Primary Examiner* — N.C. Yang

(57) ABSTRACT

Embodiments described herein may include systems and methods for detecting events that may be associated with sleep apnea. Some embodiments are directed to a system and/or method for automated detection of reduction in airflow events using polysomnograph signals, wherein the reduction in airflow events may relate to sleep apnea. The PSG signals may be limited to four signals, including data from an airflow channel, a blood oxygen saturation channel, a chest movement channel, and an abdomen movement channel. Using information from these channels, some embodiments may automatically identify reduction in airflow events.

14 Claims, 3 Drawing Sheets

U.S. PATENT DOCUMENTS

| | | |
|---|---|---|
| 5,398,682 A | 3/1995 | Lynn |
| 5,483,969 A | 1/1996 | Testerman |
| 5,485,851 A | 1/1996 | Erickson |
| 5,490,502 A | 2/1996 | Rapoport et al. |
| 5,535,739 A | 7/1996 | Rapoport et al. |
| 5,540,733 A | 7/1996 | Testerman et al. |
| 5,549,106 A | 8/1996 | Gruenke et al. |
| 5,551,419 A | 9/1996 | Froehlich et al. |
| 5,605,151 A | 2/1997 | Lynn |
| 5,632,270 A | 5/1997 | O'Mahony et al. |
| 5,645,053 A | 7/1997 | Remmers et al. |
| 5,645,054 A | 7/1997 | Cotner et al. |
| 5,682,878 A | 11/1997 | Ogden |
| 5,704,345 A | 1/1998 | Berthon-Jones |
| 5,730,144 A | 3/1998 | Katz et al. |
| 5,740,795 A | 4/1998 | Brydon |
| 5,743,250 A | 4/1998 | Gonda et al. |
| 5,749,900 A | 5/1998 | Schroeppel et al. |
| 5,751,911 A | 5/1998 | Goldman |
| 5,765,563 A | 6/1998 | Vander Schaaf |
| 5,769,084 A | 6/1998 | Katz et al. |
| 5,782,240 A | 7/1998 | Raviv et al. |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,827,179 A | 10/1998 | Lichter et al. |
| 5,830,135 A | 11/1998 | Bosque et al. |
| 5,845,636 A | 12/1998 | Gruenke et al. |
| 5,853,364 A | 12/1998 | Baker |
| 5,865,173 A | 2/1999 | Froehlich |
| 5,865,736 A | 2/1999 | Baker |
| 5,891,022 A | 4/1999 | Pologe |
| 5,891,023 A | 4/1999 | Lynn |
| 5,902,250 A | 5/1999 | Verrier et al. |
| 5,957,885 A | 9/1999 | Bollish |
| 6,006,379 A | 12/1999 | Hensley |
| 6,015,388 A | 1/2000 | Sackner et al. |
| 6,083,156 A | 7/2000 | Lisiecki |
| 6,105,575 A | 8/2000 | Estes et al. |
| 6,120,441 A | 9/2000 | Griebel |
| 6,138,675 A | 10/2000 | Berthon-Jones |
| 6,144,877 A | 11/2000 | DePetrillo |
| 6,148,814 A | 11/2000 | Clemmer et al. |
| 6,190,324 B1 | 2/2001 | Kieval et al. |
| 6,215,403 B1 | 4/2001 | Chan et al. |
| 6,216,032 B1 | 4/2001 | Griffin et al. |
| 6,223,064 B1 | 4/2001 | Lynn et al. |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,306,088 B1 | 10/2001 | Krausman et al. |
| 6,342,039 B1 | 1/2002 | Lynn et al. |
| 6,345,619 B1 | 2/2002 | Finn |
| 6,360,114 B1 | 3/2002 | Diab et al. |
| 6,367,474 B1 | 4/2002 | Berthon-Jones et al. |
| 6,371,113 B1 | 4/2002 | Tobia et al. |
| 6,375,623 B1 | 4/2002 | Gavriely |
| 6,397,092 B1 | 5/2002 | Norris et al. |
| 6,398,727 B1 | 6/2002 | Bui et al. |
| 6,401,713 B1 | 6/2002 | Hill et al. |
| 6,425,861 B1 | 7/2002 | Haberland et al. |
| 6,449,501 B1 | 9/2002 | Reuss |
| 6,463,326 B1 | 10/2002 | Hartley et al. |
| 6,488,634 B1 | 12/2002 | Rapoport et al. |
| 6,502,572 B1 | 1/2003 | Berthon-Jones et al. |
| 6,519,486 B1 | 2/2003 | Edgar, Jr. et al. |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,542,764 B1 | 4/2003 | Al-Ali et al. |
| 6,572,557 B2 | 6/2003 | Tchou et al. |
| 6,579,242 B2 | 6/2003 | Bui et al. |
| 6,609,016 B1 | 8/2003 | Lynn |
| 6,609,517 B1 | 8/2003 | Estes et al. |
| 6,622,726 B1 | 9/2003 | Du |
| 6,637,434 B2 | 10/2003 | Noble |
| 6,640,806 B2 | 11/2003 | Yurko |
| 6,641,542 B2 | 11/2003 | Cho et al. |
| 6,661,161 B1 | 12/2003 | Lanzo et al. |
| 6,675,797 B1 | 1/2004 | Berthon-Jones |
| 6,684,090 B2 | 1/2004 | Ali et al. |
| 6,691,705 B2 | 2/2004 | Dittmann et al. |
| 6,702,752 B2 | 3/2004 | Dekker |
| 6,709,402 B2 | 3/2004 | Dekker |
| 6,745,764 B2 | 6/2004 | Hickle |
| 6,748,252 B2 | 6/2004 | Lynn |
| 6,760,608 B2 | 7/2004 | Lynn |
| 6,761,167 B1 | 7/2004 | Nadjafizadeh et al. |
| 6,801,798 B2 | 10/2004 | Geddes et al. |
| 6,804,656 B1 | 10/2004 | Rosenfeld et al. |
| 6,807,965 B1 | 10/2004 | Hickle |
| 6,811,538 B2 | 11/2004 | Westbrook et al. |
| 6,814,074 B1 | 11/2004 | Nadjafizadeh et al. |
| 6,817,361 B2 | 11/2004 | Berthon-Jones et al. |
| 6,822,564 B2 | 11/2004 | Al-Ali |
| 6,830,549 B2 | 12/2004 | Bui et al. |
| 6,832,200 B2 | 12/2004 | Greeven et al. |
| 6,839,581 B1 | 1/2005 | El-Solh et al. |
| 6,896,660 B2 | 5/2005 | Jelliffe et al. |
| 6,896,661 B2 | 5/2005 | Dekker |
| 6,930,608 B2 | 8/2005 | Grajales et al. |
| 6,932,084 B2 | 8/2005 | Estes et al. |
| 6,948,497 B2 | 9/2005 | Zdrojkowski et al. |
| 6,988,498 B2 | 1/2006 | Berthon-Jones |
| 6,990,426 B2 | 1/2006 | Yoon et al. |
| 7,001,337 B2 | 2/2006 | Dekker |
| 7,031,857 B2 | 4/2006 | Tarassenko et al. |
| 7,066,173 B2 | 6/2006 | Banner et al. |
| 7,123,950 B2 | 10/2006 | Mannheimer |
| 7,153,263 B2 | 12/2006 | Carter et al. |
| 7,171,251 B2 | 1/2007 | Sarussi et al. |
| 7,210,478 B2 | 5/2007 | Banner et |
| 7,225,013 B2 | 5/2007 | Geva et al. |
| 7,246,618 B2 | 7/2007 | Habashi |
| 7,277,752 B2 | 10/2007 | Matos |
| 7,297,119 B2 | 11/2007 | Westbrook et al. |
| 7,344,497 B2 | 3/2008 | Kline |
| 7,398,115 B2 | 7/2008 | Lynn |
| 7,421,296 B1 | 9/2008 | Benser et al. |
| 2001/0018557 A1 | 8/2001 | Lynn et al. |
| 2002/0095076 A1 | 7/2002 | Krausman et al. |
| 2002/0117173 A1 | 8/2002 | Lynn et al. |
| 2003/0158466 A1* | 8/2003 | Lynn et al. .............. 600/300 |
| 2003/0163054 A1 | 8/2003 | Dekker |
| 2004/0111014 A1 | 6/2004 | Hickle |
| 2005/0016536 A1 | 1/2005 | Rapoport et al. |
| 2005/0027207 A1* | 2/2005 | Westbrook et al. ......... 600/529 |
| 2005/0081854 A1 | 4/2005 | Nadjafizadeh et al. |
| 2005/0109340 A1 | 5/2005 | Tehrani |
| 2005/0119586 A1* | 6/2005 | Coyle et al. ............... 600/538 |
| 2005/0222502 A1 | 10/2005 | Cooper |
| 2006/0155206 A1 | 7/2006 | Lynn |
| 2006/0217603 A1 | 9/2006 | Nagai et al. |
| 2006/0241506 A1 | 10/2006 | Melker et al. |
| 2006/0258921 A1 | 11/2006 | Addison et al. |
| 2006/0282001 A1 | 12/2006 | Noel et al. |
| 2007/0000494 A1 | 1/2007 | Banner et al. |
| 2007/0062531 A1 | 3/2007 | Fisher et al. |
| 2007/0100213 A1 | 5/2007 | Dossas et al. |
| 2007/0129647 A1 | 6/2007 | Lynn |
| 2007/0149871 A1 | 6/2007 | Sarussi et al. |
| 2007/0213621 A1 | 9/2007 | Reisfeld et al. |
| 2007/0282177 A1 | 12/2007 | Pilz |
| 2007/0293746 A1 | 12/2007 | Sarussi et al. |
| 2008/0076988 A1 | 3/2008 | Sarussi et al. |
| 2008/0076990 A1 | 3/2008 | Sarussi et al. |
| 2008/0076992 A1 | 3/2008 | Hete et al. |
| 2008/0082018 A1 | 4/2008 | Sackner et al. |
| 2008/0190430 A1 | 8/2008 | Melker et al. |
| 2008/0194932 A1 | 8/2008 | Ayers et al. |
| 2008/0202525 A1 | 8/2008 | Mitton et al. |
| 2008/0262326 A1 | 10/2008 | Hete et al. |
| 2008/0275349 A1* | 11/2008 | Halperin et al. ............ 600/484 |
| 2008/0295839 A1 | 12/2008 | Habashi |
| 2009/0062628 A1* | 3/2009 | Yamamoto et al. .......... 600/301 |

FOREIGN PATENT DOCUMENTS

| | | |
|---|---|---|
| EP | 0651971 A1 | 10/1995 |
| EP | 0709107 A1 | 5/1996 |
| EP | 0714670 A2 | 6/1996 |
| EP | 0722747 A2 | 7/1996 |
| EP | 0788805 A3 | 5/1998 |
| EP | 0968734 A3 | 1/2000 |
| EP | 1004325 A3 | 6/2000 |
| EP | 0700690 B1 | 2/2002 |
| EP | 0759791 B1 | 8/2002 |
| EP | 0934723 B1 | 9/2004 |
| EP | 1172123 B1 | 10/2004 |
| EP | 0875258 B1 | 11/2004 |
| EP | 1488743 A2 | 12/2004 |
| WO | WO 88/01149 | 2/1988 |
| WO | WO 90/09146 | 8/1990 |
| WO | WO 90/14121 | 11/1990 |
| WO | WO 92/11054 | 7/1992 |
| WO | WO 92/22244 | 12/1992 |
| WO | WO 94/06499 | 3/1994 |
| WO | WO 94/23780 | 10/1994 |
| WO | WO 95/32016 | 11/1995 |
| WO | WO 97/14462 | 4/1997 |
| WO | WO 97/28838 | 8/1997 |
| WO | WO 99/24099 | 5/1999 |
| WO | WO 99/45989 | 9/1999 |
| WO | 9953834 A1 | 10/1999 |
| WO | 0021438 A1 | 4/2000 |
| WO | WO 00/67827 | 11/2000 |
| WO | 0100264 A1 | 1/2001 |
| WO | 0100265 A1 | 1/2001 |
| WO | 0176471 A1 | 10/2001 |
| WO | 03000125 A1 | 1/2003 |
| WO | WO 2004/047621 A2 | 6/2004 |
| WO | 2004075746 A2 | 9/2004 |
| WO | WO 2005/065757 A1 | 7/2005 |
| WO | 2006133548 A | 12/2006 |
| WO | 2006137067 A | 12/2006 |
| WO | 2007015833 A2 | 2/2007 |

OTHER PUBLICATIONS

Aboyans, V., et al., Sleep Apnoea Syndrome and the Extent of Atherosclerotic Lesions in Middle-Aged Men with Myocardial Infarction, International Angiology, Mar. 1999, vol. 18, No. 1, pp. 70-73.

Abraham, Howard et al., Sequential Cardiorespiratory Patterns in Septic Shock, Critical Care Medicine, vol. 11, No. 10, Oct. 1983, pp. 799-803.

Agilent Technologies, Agilent M1165/66/67/75/76/77A Component Monitoring System and Agilent M1205A V24 & V26, User's Reference Manual, vol. 1, System Information, Part No. M1046-9101L, First Ed., Printed Nov. 2000.

Agilent Technologies, Agilent M1165/66/67/75/76/77A Component Monitoring System and Agilent M1205A V24 & V26, User's Reference Manual, vol. 2, Parameter Information, Part No. M1046-9101L, First Ed., Printed Nov. 2000.

Aittokallio, Tero, et al., Analysis of Inspiratory Flow Shapes in Patients with Partial Upper-Airway Obstruction During Sleep, Chest, vol. 119, No. 1, Jan. 2001, pp. 37-44, Northbrook, IL, USA.

Alchanatis, M., et al., Left ventricular function in patients with obstructive sleep apnoea syndrome before and after treatment with nasal continuous positive airway pressure, Respiration, 2000, vol. 67, No. 4, p. 367—(Abstract).

Andreas, Stefan, et al., Prevalence of Obstructive Sleep Apnoea in Patients with Coronary Artery Disease, Coronary Artery Disease, Jul. 1996, vol. 7, No. 7, pp. 541-545.

Attin, M. et al.; *An Educational Project to Improve Knowledge Related to Pulse Oximetry*; American Journal of Critical Care, Nov. 2002, vol. 11, No. 6; pp. 529-534; US.

Aubry, et al., The SaO$_2$/t Diagram as a Useful Means to Express Nocturnal Hypoxemia, Chest, 1989; 96: 1341-45.

Author Unknown, 1998 New Survey Reports More Than 168 Million American Adults Fail Sleep IQ Test, 132 Million Suffer Sleep Problems, Feb. 1998, Life Magazine.

Author Unknown, Guidance Article, (No Author), Critical Alarms and Patient Safety, Health Devices, vol. 31, No. 11, Nov. 2002, pp. 397-417, 2002 ECRI.

Author Unknown, Excessive Daytime Sleepiness, News Bulletin, http://www.websciences.org/nsf/pressarchives/leadpressrelease_g.html, Jun. 3, 1997, Washington, DC, USA.

Author Unknown, News Bulletin, Lack of sleep America's top health problem, doctors say, Health Story Page, CNN, http://cnn.com/HEALTH/9703/17/nfm/sleep.deprivation/index.html, Mar. 17, 1997.

Author Unknown, Sleep Apnea & Heart Problems, News Channel WTVC, Chattanooga, Tennessee, USA, Jun. 3, 1999, News Bulletin.

Author Unknown, The Ventilation Instability Detection Trial, Hospital Protocol, Early Discussion Draft, 4 pages, Facsimile dated Jul. 23, 2003, From SDC.

Ayas, Najib, et al., Unrecognized Severe Postoperative Hypercapnia: A Case of Apneic Oxygenation, Case Report, Mayo Clinic Proceedings, 1998, vol. 73, pp. 51-54, Minneapolis, Minnesota, USA.

Badoual, T., et al., Sleep Apnoea Syndrome and Cardiac Failure, Arch Mal Coeur Vaiss., Mar. 2005, vol. 98, No. 3, pp. 198-192, [Article in French] (Abstract).

BaHammam, A., Comparison of nasal prong pressure and thermistor measurements for detecting respiratory events during sleep, Respiration, Jul.-Aug. 2004, vol. 71, No. 4, pp. 385-390 (Abstract).

Baker, Clark R., et al., Nellcor 04 Algorithm Summary, Copyright 1999 Mallinckrodt Inc., pp. 1-8.

Ball, Eric M., et al., Diagnosis and Treatment of Sleep Apnea Within the Community, The Walla Walla Project, Arch Intern Med, vol. 157, Feb. 24, 1997, pp. 419-424.

Barach, Alvan L., et al., The Physiologic Action of Oxygen and Carbon Dioxide on the Coronary Circulation, as Shown by Blood Gas and Electrocardiographic Studies, The American Heart Journal, Received for publication Aug. 14, 1940, pp. 13-38.

Barker, Steven J., The Effects of Motion on the Performance of Pulse Oximeters in Volunteers (Revised Publication), Anesthesiology, Lippincott-Raven Publishers, American Society of Anesthesiologists, Inc.(Revised Publication) 1997, vol. 86, pp. 101-108 (Both paper and Abstract).

Barnum, P. T., et al., Novel Pulse Oximetry Technology Capable of Reliable Bradycardia Monitoring in the Neonate, Respiratory Care, 1997, vol. 42, No. 11, pp. 1072 (Abstract).

Bassetti, Claudio L., Sleep and Stroke, Seminars in Neurology, vol. 25, No. 1, Nov. 1, 2005, pp. 19-32.

Berg, Sören, et al., Continuous Intrathoracic Pressure Monitoring with a New Esophageal Microchip Catheter in Sleep-Related Upper Airway Obstructions, The Journal of Otolaryngology, vol. 24, No. 3, 1993, pp. 160-164.

Bernet-Buettiker, Vera et al., Evaluation of New Combined Transcutaneous Measurement of PCO2/Pulse Oximetry Oxygen Saturation Ear Sensor in Newborn Patients, Dec. 15, 2004, DOI: 10.1542/peds.2004-0946, Pediatrics Official Journal of the American Academy of Pediatrics, published online, pp. e-64- e68, Elk Grove Village, IL 60007, USA.

Berry, Richard B., Positive Nasal Airway Pressure Eliminates Snoring as Well as Obstructive Sleep Apnea, Chest, vol. 85, No. 1, Jan. 1984, pp. 15-20.

Berry, Richard B., et al., Comparison of Respiratory Event Detection by a Polyvinylidene Fluoride Film Airflow Sensor and a Pneumotachograph in Sleep Apnea Patients, Chest, The Cardiopulmonary and Critical Care Journal, Chest/128/3/Sep. 2005, pp. 1331-1338, Northbrook, IL, USA.

Berthon-Jones, M., et al., Time Course of Change in Ventilatory Response to CO$_2$ with Long-Term CPAP Therapy for Obstructive Sleep Apnea, American Review Respiratory Disease, 1987, vol. 135, pp. 144-147.

Berthon-Jones, Michael, Feasibility of A Self-Setting CPAP Machine, Sleep, vol. 16, pp. S120-S123, 1993.

Bixler, E. O., et al., Effects of age on sleep apnea in men: I. Prevalence and Severity, American Journal of Respiratory & Clinical Care Medicine, vol. 157, No. 1, pp. 144-148, Jan. 1998 (Abstract).

Blackshear et al., Nocturnal Dyspnea and Atrial Fibrillation Preset Cheyne—Stokes Respirations in Patients With Congestive Heart Failure, Jun. 26, 1995, Arch Intern Med. vol. 155, p. 1296-1302.

Blankfield, R. P., et al., Bilateral leg edema, obesity, pulmonary hypertension, and obstructive sleep apnea, Arch Intern Med., Aug. 14, 2000, vol. 28, 160(15), pp. 2357-2362 (Abstract).

Blankfield, R. P., et al., Bilateral leg edema, pulmonary hypertension, and obstructive sleep apnea: a cross-sectional study, Family Practice, Jun. 2002, vol. 51, No. 6, pp. 561-564 (Abstract).

Block, A. Jay, et al., Sleep Apnea, Hypopnea and Oxygen Desaturation in Normal Subjects, A Strong Male Predominance, The New England Journal of Medicine, vol. 300, Mar. 8, 1979, pp. 513-517.

Blumen, M., et al., Dilator muscles of the pharynx and their implication in the sleep apnea syndrome of obstructive type. Review of the literature., [Article in French], Ann Otolaryngol Chir Cervicofac, May 1998, p. 115 (Abstract).

Bock, A. V. et al., The Oxygen and Carbon Dioxide Dissociation Curves of Human Blood (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.

Bohnhorst, B., et al., Major Reduction in Alarm Frequency With a New Pulse Oximeter, Intensive Care Medicine, 1998, vol. 24, No. 3, pp. 277-278 (Abstract).

Bordier, P., et al., Death during polysomnography of a patient with cheyne-stokes respiration, respiratory acidosis, and chronic heart failure, Chest, Nov. 2004, vol. 126, No. 5, pp. 1698-16700 (Abstract).

Botelho, Ricardo Vieira, et al., Adult Chiari Malformation and Sleep Apnoea, Published online May 21, 2005, Neurosurgeon Review, vol. 28, pp. 169-176, 2005.

Boushra, N. N., Anaesthetic management of patients with sleep apnoea syndrome, Canadian Journal Anaesth, Jun. 1996, vol. 45, No. 6, pp. 599-616 (Abstract).

Bowton, David L., et al., The Incidence and Effect on Outcome of Hypoxemia in Hospitalized Medical Patients, The American Journal of Medicine, Vo. 97, Jul. 1994, pp. 38-46.

Bradley, Douglas T., et al., Daytime Hypercapnia in the Development of Nocturnal Hypoxemia in COPD, Chest, vol. 97, No. 2, Feb. 1990, pp. 308-312.

Brooks, L. J., et al., Adenoid size is related to severity but not the number of episodes of obstructive apnea in children, Journal of Pediatrics, vol. 132, No. 4, pp. 682-686, Apr. 1998 (Abstract).

Broughton, Roger J., et al., Practice Parameters for the Use of Stimulants in the Treatment of Narcolepsy, ASDA Standards of Practice, Sleep, vol. 17, No. 4, pp. 348-351, American Sleep Disorders Association and Sleep Research Society 1994.

Brown, Lee K., "Dephlogisticated air" revisited: oxygen treatment for central sleep apnea, 1997 American College of Chest Physician, Physician Information, No. 8, Rev. 01, Nov. 1997.

Brown, D. L., et al., Screening for obstructive sleep apnea in stroke patients: a cost-effectiveness analysis, Stroke, Jun. 2005, pp. 1291-1293, Epub May 12, 2005 (Abstract).

Burk, John R., et al., Auto-CPAP in the Treatment of Obstructive Sleep Apnea: A New Approach, Sleep Research 21, 1992, p. 182, Abstract.

Cain, S. M., Breaking Point of Two Breath Holds Separated by a Single Inspiration, Journal of Appl. Physiol., vol. II(I), Jul. 1957, pp. 87-90.

Campos-Rodriguez, Francisco, et al., Mortality in Obstructive Sleep Apnea-Hypopnea Patients Treated With Positive airway Pressure, Chest, The Cardiopulmonary and Critical Care Journal, 2005, vol. 128, pp. 624-633, Northbrook, Illinois, USA (plus Abstract).

Cannesson, Maxime et al., Relation between respiratory variations in pulse oximetry plethsmographic waveform amplitude and arterial pulse pressure in ventilated patients, Critical Care 2005, vol. 9, #5, pp. R562-R568, Available online http://ccforum.com/content/9/5/R562.

Chaoquat, Ari, et al., Association of Chronic Obstructive Pulmonary Disease and Sleep Apnea Syndrome, American Journal Respiratory Critical Care Medicine, 1995, vol. 151, pp. 82-86.

Cherniack and Longobardo, Periodic Breathing During Sleep, pp. 158-190, New Jersey Medical School, Dean's Office, ID 9739727104, May 26, 1999, 14:23, No. 010, (first page missing).

Cherniack, N. S., Introduction to Session on the Pathophysiology of Breathing Control and Breathing: Awake and Asleep, Modeling and Control of Ventilation, Plenum Press, New York, USA, 1995, pp. 87-88.

Cherniack, N. S., New mechanisms for the cardiovascular effects of sleep apnea, American Journal Medicine, Nov. 1, 2000, vol. 109, No. 7, pp. 592-594 (Abstract).

Cherniack, Neil S., Oxygen Sensing: applications in humans, Highlighted Topic: Oxygen Sensing in Health and Disease, Journal Appl. Physiol., vol. 96, pp. 352-358, 2004, The American Physiological Society, http://www.jap.org.

Christiansen, J., et al., Carbon Dioxide in Blood, pp. 266-271, Proceedings of the Physiological Society, This Journal, XLVII, p. ii, 1913, pp. 266-271.

Cilli, Aykut, et al., Nocturnal Oxygen Desaturation in Coronary Artery Disease, JPN Heart Journal, Jan. 1999, pp. 23-28.

CNS Poly G, Printout Examples, CNS, Inc., Chanhassen, Minnesota, USA, Undated, Test Date Feb. 10, 1992.

Conte, G., et al., Acute cardiovascular diseases and respiratory sleep disorders, Minerva Cardioangiol, Jun. 1999, vol. 47, No. 6, pp. 195-202 (Abstract).

Cooper, B. G., et al., Value of Nocturnal Oxygen Saturation As a Screening Test for Sleep Apnoea, Thorax, 1991, vol. 46, pp. 586-588.

Coppola, Michael P., et al., Management of Obstructive Sleep Apnea Syndrome in the Home, The Role of Portable Sleep Apnea Recording, Chest, vol. 104, No. 1, Jul. 1993, pp. 19-24, Northbrook, IL, USA.

Coy, Timothy V., Sleep Apnoea and Sympathetic Nervous System Activity: A Review, Journal Slep Res., 1996, No. 5, pp. 42-50, European Sleep Research Society.

Decker, Michael J., et al., Ambulatory Monitoring of Arterial Oxygen Saturation, Chest, vol. 95, No. 4, Apr. 1989, pp. 717-722, Northbrook, Illinois, USA.

Deegan, P. C., et al., Predictive Value of Clinical Features for the Obstructive Sleep Apnoea Syndrome, European Respiratory Journal, vol. 9, pp. 117-124, 1996.

DeLeeuw, P.W., On sleep and death: cardiovascular risk the obstructive sleep apnea syndrome, Neth Journal Medicine, May 1999, vol. 54, No. 5, pp. 188-190 (Abstract).

Dement, William C., Chairman, National Commission on Sleep Disorders Research, Wake Up America: A National Sleep Alert, vol. 1, Executive Summary and Executive Report, Report of the National Commission on Sleep Disorders Research, Submitted to the United States Congress and to the Secretary, u.s. department of Health and Human Services, Jan. 1993, pp. 1-76.

Demeter, P., et al., The relationship between gastroesophageal reflex disease and obstructive sleep apnea, Gastroenterology, Sep. 2004, vol. 39, No. 9, pp. 815-820 (Abstract).

Dempsey, Jerome A., et al., Sleep and Breathing State of the Art Review Sleep-Induced Breathing Instability, Sleep, vol. 19, No. 3, pp. 236-247, American Sleep Disorders Association and Sleep Research Society.

Den Herder, Cindy et al., Risks of general anaesthesia in people with obstructive sleep apnea, BMJ, vol. 329, Oct. 23, 2004, pp. 955-959, Downloaded from bmj.com.

Dhonneur, G., et al., Postoperative Obstructive Apnea, Anesth Analg., Sep. 1999, vol. 89, No. 3, pp. 762-767 (Abstract).

Doherty, L. S, et al., Long-term effects of nasal continuous positive airway pressure therapy on cardiovascular outcomes in sleep apnea syndrome, Chest, Jun. 2005, vol. 127, No. 6, pp. 2076-2084 (Abstract).

Douglass, Alan B., et al., The Sleep Disorders Questionnaire I. Creation and Multivariate Structure of SDQ, Clinical Research, Sleep, vol. 17, No. 1, pp. 160-167, 1994 American Sleep Disorders Association and Sleep Research Society.

Dowdell, WT; Javaheri, S; McGinnis, W, Cheyne-Stokes Respiration Presenting as Sleep Apnea Syndrome. Clinical and Polysomnographic Features, Am Rev Respir Dis, Apr. 1990, pp. 871-879.

Downs, John B., Has Oxygen Administration Delayed Appropriate Respiratory Care? Fallacies Regarding Oxygen Therapy, Respiratory Care, Jun. 2003, vol. 48, No. 6.

Downs, John B., Is Supplemental Oxygen Necessary, Journal of Cardiothoracic and Vascular Anesthesia, vol. 20, No. 2, Apr. 2006.

Dumas, Constantine, et al., Clinical Evaluation of a Prototype Motion Artifact Resistant Pulse Oximeter in the Recovery Room, Anesth Analg 1996, vol. 83, pp. 269-272.

Dursunoglu, D., et al., Impact of obstructive sleep apnoea on left ventricular mass and global function, European Respiratory Journal, Aug. 2005, vol. 26, No. 2, pp. 283-288 (Abstract).

Dyken, M. E., et al., Obstructive sleep apnea associated with cerebral hypoxemia and death, Neurology, Feb. 10, 2004, vol. 62, No. 3, pp. 491-493 (Abstract).

Dziewas, R., et al., Capnography screening for sleep apnea in patients with acute stroke, Neurology Res. Jan. 2005, vol. 27, No. 1, pp. 83-87 (Abstract).

Dziewas, R., et al., Increased Prevalence of Sleep Apnea in Patients with Recurring Ischemic stroke Compared with First Stroke Victims, Journal Neurology, Nov. 2005, vol. 252, No. 11, pp. 1394-1398. Epub Jul. 20, 2005 (Abstract).

Edge City Hospital Sleep Disorders Center, Sleep Summary of Patient, Houston, Texas, USA, pp. 1-3, Feb. 17, 1997.

Elfadel, I. M., et al., Motion-Resistant Pulse Oximetry, Abstract Only, Journal of Clinical Monitoring, vol. II, No. 4, Jul. 1995, p. 262.

Eihefnawy, Ahmed, et al., Stability Analysis of CO2 Control of Ventilation, Journal of Internal Medicine, 0161-7567/90, pp. 498-503, Publisher: The American Physiological Society, 1990.

Epstein et al., "Cost-Effectiveness Analysis of Nocturnal Oximetry As a Method of Screening for Sleep Apnea-Hypopnea Syndrome," Jan. 1, 1998, Chest, vol. 113, p. 97-103.

Escourrou, P., et al., Heart failure and sleep respiratory disorders. Prevalence, physiopathology and treatment, [Article in French], Rev Mal Respir, Jun. 2000, vol. 17, Suppl 3, pp. S31-40 (Abstract).

Evans, et al., A Microcomputer System for Monitoring and Analysing Oxyhemolobin Saturation During Sleep. Computer Programs in Biomedicine, 1984; 18: 227-234.

Farhi, Leon E., et al., Dynamics of Changes in Carbon Dioxide Stores, Anesthesiology, Nov.-Dec. 1960, vol. 21, pp. 604-614 (last page missing).

Farney, Robert J., et al., Ear Oximetry to Detect Apnea and Differentiate Rapid Eye Movement (REM) and Non-REM (NREM) Sleep, Screening for the Sleep Apnea Syndrome, Chest, vol. 89, No. 4, Apr. 1986, pp. 533-539, Northbrook, IL, USA.

Farre, R., et al., Importance of the Pulse Oximeter Averaging time When Measuring Oxygen Desaturation in Sleep Apnea, Sleep, Jun. 15, 1998, vol. 21, No. 4, pp. 386-390 Missing pp. 386 and 390.

Feinsilver, Steven H., Current and Future Methodology for Monitoring Sleep, Sleep Disorders, Clinics in Chest Medicine, vol. 19, No. 1, Mar. 1998, Published from the Division of Pulmonary Medicine, North Shore University Hospital, Manhasset, New York, NY, USA.

Findley, Larry J., et al., Cheyne-Stokes Breathing During Sleep in Patients With Left Ventricular Heart Failure, Southern Medical Journal, vol. 78, No. 1, Jan. 1985, pp. 11-15.

Findley, Larry J., et al., Sleep Apnea and Auto Crashes, What is the Doctor to do?, Chest, vol. 94, No. 2, Aug. 1988, pp. 225-226.

Fiz, J. A., et al., Acoustic Analysis of Snoring Sound in Patients with Simple Snoring and Obstructive Sleep Apnoea, European Respiratory Journal, 1996, vol. 9, pp. 2365-2370, Printed in the United Kingdom.

Flemons, W. Ward, et al., Sleep Apnea and Cardiac Arrhythmias, Is There a Relationship?, American Review Respiratory Disease, vol. 148, pp. 618-621, 1993.

Fletcher et al., Effect of Cardiac Output Reduction on Rate of Desaturation in Obstructive Apnea; Chest, 99:452-456, 1991.

Fletcher et al., Rate of Oxyhemolglobin Desaturation in Obstructive versus Nonobstructive Apnea; Am Rev Respi Dis. 143:657-660; 1990.

Fletcher et al., The Rate of Fall of Arterial Oxyhemoglobin Saturation in Obstructive Sleep Apnea, Chest, 1989; 96: 717-722.

Fletcher, Eugene C., et al., Nocturnal Oxyhemoglobin Desaturation in COPD Patients with Arterial Oxygen Tensions Above 60 mm Hg, Chest, vol. 92, No. 4, Oct. 1987, pp. 604-608.

Forster, R. E., et al., Time course of exchanges between red cells and extracellular fluid during $CO_2$ uptake, Journal of Applied Physiology, vol. 38, No. 4, Apr. 1975, Printed in U.S.A.

Forster, Robert E., The Lung: Physiologic Basis of Pulmonary Function Tests (Book), 1986 Year Book medical Publishers, Inc., Chapter 3, I. vol. of Pulmonary Ventilation, pp. 32-64.

Franklin, K. A., et al., Reversal of Central Sleep Apnea with Oxygen, Chest, Jan. 1997, vol. 111, No. 1, pp. 163-169 (Abstract).

Freid, E. B. The rapid sequence induction revisited: obesity and sleep apnea syndrome, Anesthesiol Clin North America, Sep. 2005, vol. 23, No. 3, pp. 551-564 (Abstract).

Frumin, Jack M., Apneic Oxygenation in Man, Anesthesiology, vol. 20, pp. 789-798, 1959.

Fu, Eugene S., et al., Supplemental Oxygen Impairs Detection of Hypoventilation by Pulse Oximetry, Chest 2004; vol. 126, pp. 1552-1558.

Gagnadoux, Fredrick et al., Home Unattended vs Hospital Telemonitored Polysomnography in Suspected Obstructive Sleep Apnea Syndrome: A Randomized Crossover Trial, Chest 2002; 121; 753-758.

Gami, A. et al., Day-night pattern of sudden death in obstructive sleep apnea, New England Journal Medicine, Mar. 24, 2005, vol. 352, No. 12, pp. 1206-1214.

Gangitano, E. S., et al., Near Continuous Pulse Oximetry During Newborn ECLS, ASAI Journal, 1999, vol. 45, No. 1, p. 125 (Abstract).

Gaultier, C., Upper airway muscles and physiopathology of obstructive sleep apnea syndrome, [Article in French], Neurophysiol Clin, Jun. 1994, vol. 24, No. 3, pp. 195-206 (Abstract).

Gavin, T. P., et al.,The effect of exercise modality on exercise-induced hypoxemia, Respiration Physiology, May 3, 1999, vol. 115, No. 3, pp. 317-323 (Abstract).

Gentil, Benoit, et al., Enhancement of Postoperative Desaturation in Heavy Snorers, Anesth Analg 1995, vol. 81, pp. 389-392.

George et al., Identification on Qualification of Apneas by Computer-based Analysis of Oxygen Saturation, American Review of Respiratory Disease, 1988; 137; 1238-1240.

George, Charles Frederick Petersen, Diagnostic Techniques in Obstructive Sleep Apnea, Progress in Cardiovascular Diseases, vol. 41, No. 5, Mar./Apr. 1999, pp. 355-366.

Glerant, J. C., et al., Intensive care and respiratory sleep disorders, [Article in French], Rev Mal Respir, Dec. 1999, vol. 16, No. 6, pp. 1091-1104 (Abstract).

Gold, Avram R., et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL, USA.

Goldberger, Ary L., et al., Components of a New Reserarch Resource for Complex Physiologic Signals, PhysioBank, Physio Toolkit, and PhysioNet. American Heart Association Journals, Circulation, vol. 101, No. 23, pp. 1-9, 2000, Circulation, 2000:101:e215, http://circ.ahajournals.org/cgi/content/ful/101/23/e215.

Goldstein, M. R., et al., Pulse Oximetry in Transport of Poorly-Perfused Babies, Abstract only, Pediatrics, 1998, vol. 102, No. 3, p. 818.

Goode, Richard L., Who needs a sleep test? The value of the history in the diagnosis of obstructive sleep apnea, http://www.findarticles.com/p/articles/mi_m0BUM/is_9_78/ai_56229331/print, Sep. 1999.

Goodfriend, Theodore L., et al., Resistant Hypertension, Obesity, Sleep Apnea, and Aldosterone: Theory and Therapy, Hypertension, Journal of the American Heart Association, published online Jan. 19, 2004, Print ISSN: 0194-911X. Online ISSN: 1524-4563, pp. 518-524, Dallas, Texas, USA.

Grap, Mary Jo, Protocols for Practice, Applying Research at the Bedside, Critical Care Nurse, vol. 18, No. 1, Feb. 1998, pp. 94-99.

Greco, J. M., et al., Long-term Airway Space Changes after Mandibular Setback Using Bilateral Sagittal Split Osteomy, Internal Journal Oral Maxillofac. Surg. 1990, vol. 19, pp. 103-105.

Greco, Joan M., Cephalometric Analysis of Long-Term Airway Space Changes with Maxillary Osteotomies, Oral Surg Oral Med Oral Pathol, Nov. 1990, vol. 70, No. 5, pp. 552-554.

Griffiths, et al., A Video System for Investigating Breathing Disorders During Sleep, Thorad, 1991; 46: 136-140.

Grimm, W., et al., Outcome of patients with sleep apnea-associated severe bradyarrhythmias after continuous positive airway pressure therapy, American Journal Cardiology, Sep. 15, 2000, vol. 86, No. 6, pp. 688-692 (Abstract).

Grote, Ludger, et al., Finger Plethysmography—A Method for Monitoring Finger Blood Flow During Sleep Disordered Breathing, Respiratory Physiology & Neurobiology, vol. 136, 2003, pp. 141-152, Publisher: Elsevier.

Grunstein, Ronald R., et al., Treatment of Sleep Disordered Breathing, Position Statement, The Medical Journal of Australia, vol. 154, Mar. 4, 1991, pp. 355-359, Australia.

Gugger, M., Comparison of ResMed AutoSet (version 3.03) with polysomnography in the diagnosis of the sleep apnoea/hypopnoea syndrome, European Respiratory Journal, Mar. 1997, vol. 10, No. 3, pp. 587-591 (Abstract).

Guilleminault et al., Sleep Apnea Syndrome: Can It Induce Hemodynamic Changes?, Western Journal of Medicine, vol. 123, Jul. 1975, pp. 7-16.

Guilleminault, C. et al., Unattended CPAP Titration: Toward A Smart Machine, May 20, Stanford University Sleep Research Center, 1 page.

Guilleminault, C., et al., Maxillo-mandibular surgery for obstructive sleep apnoea, European Respiratory Journal, 1989, vol. 2, pp. 604-612.

Guilleminault, C., et al., Sleep-disordered breathing in children, Annals of Medicine, vol. 30, No. 4, pp. 350-356, Aug. 1998 (Abstract).

Guilleminault, Christian, et al., A Cause of Excessive Daytime Sleepiness, The Upper Airway Resistance Syndrome, Chest, vol. 104, No. 3, Sep. 1993, pp. 781-787.

Guilleminault, Christian, et al., The Sleep Apnea Syndromes, Copyright 1976, Citation Annual Review of Medicine, vol. 27: 465-484 (Volume publication date Feb. 1976).

Guilleminault, Christian, Obstructive Sleep Apnea, The Clinical Syndrome and Historical Perspective, Medical Clinics of North America, vol. 69, No. 6, Nov. 1985, pp. 1187-1203, Stanford, California, USA.

Gupta, R. M., et al., Perioperative cardiopulmonary evaluati and management: are we ignoring obstructive sleep apnea syndrome?, chest, Dec. 1999, vol. 116, No. 6, p. 1843 (Abstract).

Gupta, Rakesh M., et al., Postoperative Complications in Patients with Obstructive Sleep Apnea Syndrome Undergoing Hip or Knee Replacement: A Case-Control Study, Mayo Clinic Proceedings, 2001, vol. 76, pp. 897-905, Rochester, MN, USA.

Gyulay et al., A Comparison of Clinical Assessment and Home Oximetry in the Diagnosis of Obstructive Sleep Apnea, American Review of Respiratory Disease, 1993; 147: 50-53.

Gyulay, Stephen, et al., Evaluation of a Microprocessor-Based Portable Home Monitoring System to Measure Breathing During Sleep, Sleep, vol. 10, No. 2, pp. 130-142, Raven Press, New York, USA, 1987, Association of Professional Sleep Societies.

Hanley, Patrick, et al., Pathogenesis of Cheyne-Stokes Respiration in Patients with Congestive Heart Failure, Relationship to Arterial $Pco_2$, Chest, vol. 104, No. 4, Oct. 1993, pp. 1079-1084.

Hanly, P. J., et al., Increased Mortality Associated with Cheyne-Stokes Respiration in Patients with Congestive Heart Failure, American Journal Respiratory Critical Care Medicine, Jan. 1996, vol. 153, No. 1, 272-6 (Abstract).

Hanly, Patrick J., et al., Respiration and Abnormal Sleep in Patients with Congestive Heart Failure, Chest, vol. 96, No. 3, Sep. 1989, pp. 480-488.

Hanly, Patrick, et al., ST-Segment Depression During Sleep in Obstructive Sleep Apnea, The American Journal of Cardiology, vol. 71, Jun. 1, 1993, pp. 1341-1345.

Harbison, J., et al., Cardiac rhythm disturbances in the obstructive sleep apnea syndrome: effects of nasal continuous positive airway pressure therapy, Chest, Sep. 2000, vol. 118, No. 3, pp. 591—(Abstract).

Hatta, K., et al., Prolonged upper airway instability in the parenteral use of benzodiazepine with levomepromazine, Journal Clin Psychopharmacol, Feb. 2000, vol. 20, No. 1, pp. 99—(Abstract).

He, Jiang, et al., Mortality and Apnea Index in Obstructive Sleep Apnea, Experience in 385 Male Patients, Clinical Investigations, Chest, vol. 94, No. 1, Jul. 1988, pp. 9-14.

Health Devices, Next-Generation Pulse Oximetry, Special Issue, Feb. 2003, vol. 32, No. 2, Plymouth Meeting, PA, USA.

Henderson, L. J., et al., Blood as a Physicochemical System. II, pp. 426-431, Paper.

Hillman, David R., et al., Obstructive Sleep Apnoea and Anaesthesia, Sleep Medicine Reviews, 2004, vol. 8, pp. 459-472, Publisher: Elsevier.

Hoch, et al., Uberprufung der Fruherkennungsmethode MESAM and Biox 3700 zur Erfassung Schlafbezogener Atmmgmsergulationsstorungen bei jungen Mannern, Pneumologie, 1991; 45: 217-222 (and translation).

Hoffarth, et al., Beuteilung Pulsoximetrisch Erfasster zklisheer.. and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229-232.

Hoffman, Eric A., et al., Multimodality Imaging of the Upper Airway: MRI, MR Spectroscopy, and Ultrafast X-ray CT, Sleep and respiration, 1990 Wiley-Liss, Inc., pp. 291-301.

Hoffmann, M., et al., Sleep apnea and hypertension, Minerva Med., Aug. 2004, vol. 95, No. 4, pp. 281-290 (Abstract).

Hoffstein, Victor, Blood Pressure, Snoring, Obesity, and Nocturnal Hypoxaemia, The Lancet, vol. 344, Sep. 3, 1994, pp. 643-645.

Hoffstein, Victor, et al., Cardiac Arrhythmias, Snoring, and Sleep Apnea, Chest, 1994, vol. 106, pp. 466-471, Northbrook, IL, USA.

Hoffstein, Victor, et al., Snoring and Arousals: A Retrospective Analysis, Sleep, vol. 18, No. 10, pp. 866-882, 1995 American Sleep Disorders Association and Sleep Research Society.

Holmes, Michael, et al., Co-Oximetry Validation of a New Pulse Oximeter in Sick Newborns, Respiratory Care, 1998, vol. 43, No. 10, pp. 860 (Abstract).

Howell, Mandy et al.; *Pulse oximetry: an audit of nursing and medical staff understanding*; British Journal of Nursing, 2002, vol. 11, No. 3; pp. 191-197.

Hornero, Roberto, et al.; "Utility of Approximate Entropy From Overnight Pulse Oximetry Data in the Diagnosis of the Obstructive Sleep Apnea Syndrome,"; *IEEE Transactions on Biomedical Engineering*, vol. 54, No. 1, pp. 107-113, Jan. 2007.

Hung, Joseph, et al., Association of Sleep Apnoea with Myocardial Interfarction in Men, The Lancet, vol. 336, pp. 261-264, Jul. 28, 1990, Abstract only, p. 261.

Isono, S., et al., Anatomy of pharynx in patients with obstructive sleep apnea and in normal subjects, Journal Appl Physiol, Apr. 1997, vol. 82, No. 4, pp. 1319-1326 (Abstract).

Isono, S., et al., Interaction of cross-sectional area, driving pressure, and airflow of passive velopharynx, Journal Appl Physiol, Sep. 1997, vol. 83, No. 3, pp. 851-859 (Abstract).

Isono, S., et al., Static mechanics of the velopharynx of patients with obstructive sleep apnea, Journal Appl Physiol, Jul. 1999, vol. 75, No. 1, pp. 148-154 (Abstract).

Jain, Sanjay S., et al., Perioperative Treatment of Patients with Obstructive Sleep Apnea, Current Opinion Pulmonary Medicine 10, pp. 482-488.

Jarrell, L., Preoperative diagnosis and postoperative management of adult patients with obstructive sleep apnea syndrome: a review of the literature, Journal Perianesth Nursing, Aug. 1999, vol. 14, No. 4, pp. 193-200 (Abstract).

Javaheri, S., Effects of continuous positive airway pressure on sleep apnea and ventricular irritability in patients with heart failure, Circulation, Feb. 1, 2000, vol. 101, No. 4, pp. 392-397 (Abstract).

Javaheri, S., et al., Occult Sleep-Disordered Breathing in Stable Congestive Heart Failure, Annuals Internal Medicine, Apr. 1995, vol. 122, No. 7, pp. 487-492 (Abstract).

Javaheri, S., et al., Sleep Apnea in 81 Ambulatory Male Patients With Stable Heart Failure, Types and Their Prevalences, Consequences, and Presentations, Received Nov. 20, 1997; revision received Jan. 23, 1998, accepted Jan. 28, 1998, From the Sleep Disorders Laboratory, Department of Veterans Affairs Medical Center, and the Department of Medicine, University of Cincinatti, College of Medicine, Cincinnati, Ohio.

Johnson, J. T., et al., Preoperative, Intraoperative, and postoperative management of patients with obstructive sleep apnea syndrome, Otolaryngol Clin North America, Dec. 1998, vol. 31, No. 6, pp. 1025-1030 (Abstract).

Jones, N. L., et al., The Estimation of Carbon Dioxide Pressure of Mixed Venous Blood During Exercise, Clinical Science (1967), vol. 32, pp. 311-327.

Juhász, János, et al., Unattended Continuous Positive Airway Pressure Titration, Clinical Relevance and Cardiorespiratory Hazards of the Method, American Journal Respiratory Critical Care Medical, vol. 154, pp. 359-365, 1996.

Kabeli, Cheryl, Obstructive Sleep apnea and Modifications in Sedation, Critical Care Nursing Clinics of North America, vol. 17, 2005, pp. 269-277, ccnursing.theclinics.com, Publisher: Elsevier Saunders.

Kalra, Maninder, et al., Obstructive Sleep Apnea in Extremely Overweight Adolescents Undergoing Bariatric Surgery, Obesity Research, vol. 13, No. 7, Jul. 2005, pp. 1175-1179.

Kanagala, Ravi, et al., Obstructive Sleep Apnea and the Recurrence of Atrial Fibrillation, Circulation, May 27, 2003, pp. 2589-2594, American Heart Association, Inc.

Kaplan, Joseph, Beginner's Atlas of Overnight Oximetry, Apr. 10, 1995, Mayo Clinic, Jacksonville, Florida, USA, Copyright 1986, PROFOX Associates, Inc.

Kaplan, Joseph, et al., Home Pulse Oximetry As a Screening Test for Sleep-Disordered Breathing, Chest, vol. 103, pp. 322S, (1993) Northbrook, IL, USA.

Kapur, V. K., et al., Association of hypothyroidism and obstructive sleep apnea, American Journal of Respiratory & Critical Care Medicine, vol. 158, No. 5 Pt. 1, pp. 1379-1383, Nov. 1998 (Abstract).

Kapur, V., et al., The medical cost of undiagnosed sleep apnea, Sleep, Sep. 1999, vol. 22, No. 6, pp. 749-755 (Abstract).

Katchen, Marc, et al., Evaluation of the Sleepy Crewmember: USAFSAM Experience and a Suggested Clinical Approach, Aviation, Space and Environmental Medicine, Mar. 1989, pp. 263-267.

Kaw, Roop, et al., Unrecognized Sleep Apnea in the Surgical Patient, Implications for the Perioperative Setting, Chest, 2006, vol. 129, pp. 198-205.

Kawai, Mitsuru, et al., Nocturnal hypoxia index: A new pulse oxymetry index of nocturnal hypoventilation in neuromuscular disorders, Clinical Neurology, vol. 35, pp. 1003-1007, 1995 (Abstract).

Keyl, C., et al., Spektralanalyse von Arterieller Sauerstoff-sättigung und RR-Intervallen bei Patienten mit obstrukitver Schlafapnoe, Wein Med Wschr 1995, pp. 515-516 (vol. 145).

Kimmel, Paul L., et al., Sleep Apnea syndrome in Chronic renal Disease, The American Journal of Medicine, vol. 86, Mar. 1989, pp. 308-314.

King, E. D., et al., A model of obstructive sleep apnea in normal humans. Role of the upper airway., American Journal Respiratory Critical Care Medicine, Jun. 2000, vol. 161, No. 6, pp. 1979-1984 (Abstract).

Kirby et al., Computer Quantitation of Saturation Impairment Time As an Index of Oxygenation During Sleep, Com Meth, 1992: 107-115.

Kirby, S.D., et al., Neural network prediction of obstructive sleep apnea from clinical criteria, Chest, vol. 116, No. 2, pp. 409-415, Aug. 1999 (Abstract).

Kirby, Stan C., et al., Section II. Systems and programs, Computer quantitation of saturation impairment time as an index of oxygenation during sleep, Computer Methods and Programs in Biomedicine, vol. 38, 1992, pp. 107-115, Elsevier Science Publishers B.V.

Klocke, F. J., et al., Breath holding after breathing of oxygen, Journal Appl. Physiol., vol. 14, No. 5, pp. 689-693, 1959.

Koehler, U., et al., Heart Block in Patients with Obstructive Sleep Apnoea: Pathogenetic Factors and Effects of Treatment, European Respiratory Journal, 1998, vol. 11, pp. 434-439, Printed in United Kingdom.

Koehler, U., et al., Nocturnal Myocardial Ischemia and Cardiac Arrhythmia in Patients with Sleep Apnea with and Without Coronary Heart Disease (1991) 69; 474-482.

Kolobow, Theodor, et al., Intratracheal Pulmonary Ventilation (ITPV); Control of Positive End-Expiratory Pressure at the Level of the Carina Through the Use of a Novel ITPV Catheter Design, Anesth Analg, 1994, vol. 78, pp. 455-461.

Koopmann, Charles F., et al., Surgical Management of Obstructive Sleep Apnea, Otolaryngologic Clinics of North America, vol. 23, No. 4, Aug. 1990, pp. 787-808.

Krachman, S. L., et al., Comparison of oxygen therapy with nasal continuous positive airway pressure on Cheyne-Stokes respiration during sleep in congestive heart failure, Chest, Dec. 1999, vol. 116, No. 6, pp. 1550-1557 (Abstract).

Kribbs, Nancy Barone, et al., Effects of One Night without Nasal CPAP Treatment on Sleep and Sleepiness in Patients with Obstructive Sleep Apnea, American Review Respiratory Disease, vol. 147, pp. 1162-1168, 1993.

Kribbs, Nancy Barone, et al., Objective Management of Patterns of Nasal CPAP Use by Patients with Obstructive Sleep Apnea, American Review Respiratory Disease, vol. 147, pp. 887-895, 1993.

Krieger, Jean, et al., Breathing During Sleep in Normal Middle-Aged Subjects, Sleep, vol. 13, No. 2, pp. 143-154, Raven Press, Ltd. New York, NY, USA, 1990 Association of Professional Sleep Societies.

Krieger, Jean, et al., Left Ventricular Ejection Fraction in Obstructive Sleep Apnea, Effects of Long-term Treatment with Nasal Continuous Positive Airway Pressure, Chest, vol. 100, No. 4, Oct. 1991, pp. 917-921.

Krieger, Jean., et al., Dangerous Hypoxaemia During Continuous Positive Airway Pressure Treatment of Obstructive Sleep Apnoea, The Lancet, Dec. 17, 1983, pp. 1429-1430.

Kuna, S. T., et al., Pathophysiology of upper airway closure during sleep, JAMA, Sep. 11, 1991, vol. 266, No. 10, pp. 1384-1389 (Abstract).

Kyzer, S., et al., Obstructive Sleep Apnea in the obese, World Journal Surg, Sep. 1988, vol. 22, No. 9, pp. 998-1001 (Abstract).

LaFontaine, Victoria M., et al., Pulse Oximetry: Accuracy of Methods of Interpreting Graphic Summaries, Pediatric Pulmonology, vol. 21, 1996, pp. 121-131.

Lanfranchi, P. A., et al., Prognostic value of nocturnal Cheyne-Stokes respiration in chronic heart failure, Circulation, Mar. 23, 1999, vol. 99, No. 11, pp. 1435-1440, Italy (Abstract).

Lanfranchi, P., et al., The assessment of breathing during sleep: a curiosity or clinical necessity?, Italian Heart Journal, May 2000, vol. 1, No. 5 Suppl., pp. 641-654 (Abstract).

Lawrence, Nancy, Treatment for Sleep Apnea shows promise in reducing deaths from congestive heart failure: Nation-wide study to determine long-term benefits, London Health Sciences Centre, Jun. 3, 1999, News Bulletin.

Lertzman, Morley, et al., [Letters—Correspondence], Sleep Apnea A Risk Factor for Poor Driving, Canadian Medical Association Journal, Oct. 15, 1995; vol. 153(8), p. 1063.

Letters, Obstructive Sleep Apnoea, BMJ, 1997, pp. 315-367 (Aug. 9); http://bmj.com/Shneerson et al. (7104).

Lichstein, K. L., et al., Occult sleep apnea in a recruited sample of older adults with insomnia, Journal of Consulting & Clinical Psychology, vol. 67, No. 3, pp. 405-410, Jun. 1999 (Abstract).

Little, S. A., et al., Predictors of nocturnal oxygen desaturation in patients with COPD, Respir Med., Mar. 1999, vol. 93, No. 3, pp. 202-207, United Kingdom (Abstract).

Lofsky, Ann, Sleep Apnea and Narcotic Postoperative Pain Medication: A Morbidity and Mortality Risk, APSF Newsletter Summer 2002, pp. 24-25.

Longobardo et al., Sleep Apnea Considered As a Control System Instability, Sep. 1982, Respiratory Physiology 50: 311-333.

Longobardo, G. S., et al., Sleep Apnea Considered As a Control System Instability, Elsevier Biomedical Press, 1982, 0034-5687/82/0000-0000.

Lowton, K., Pulse oximeters for the detection of hypoxaemia, Professional Nurse, Feb. 1999, vol. 14, No. 5, pp. 343-347 (Abstract).

Lugaresi, E., et al., Breathing During sleep in Man in Normal and Pathological Conditions, Proceedings of the Symposium on Regulation of Respiration during Sleep and Anesthesia held at the Faculte de Medecine Saint-Antoine, Paris, France, Jul. 14-16, 1977, 1978 Plenum Press, New York, USA, pp. 35-45.

Lynn, Lawrence A. et al., Diagnostic Evaluation of OSA Utilizing Analysis of Frequency and Spatial Relationships of Clustered, Sequential Oximetry Waveform Events, Vth World Congress on Sleep Apnea, Marburg, Germany, Sep. 17-20, 1997.

Lynn, Lawrence A., Cluster Analysis: A New Technology for the Evaluation of Oximetry and Airflow Waveforms in Obstructive Sleep Apnea, Accepted after revision on Dec. 20, 1997, 17 total pages.

Lynn, Lawrence, PROFOX Associates, Inc., Version 12S (12 hours SpO2), Demonstration disk for Dr. Lawrence Lynn, Columbus, Ohio, Copyright 1986 PROFOX Associates, Inc., Version 12S, Nov. 1992, p. 1.

Lynn, Lawrence A., Interpretive Oximetry: Future Directions for Diagnostic Applications of the $SpO_2$ Time-Series, Anesth Analg 2002, vol. 94, pp. S84-S88.

Lynn, Lawrence; *Piercing the Panacea of Pulse Oximetry*; The Sleep and Breathing Research Institute, Columbus, Ohio, US.

Lyznicki, James M., Sleepiness, Driving and Motor Vehicle Crashes, JAMA, Jun. 17, 1998, vol. 279, No. 23, pp. 1908-1913.

Mackenzie, I.M.J.; *The haemodynamics of human septic shock*; Anaesthesia; 2001; 56; pp. 130-144; UK.

Magalang, Ulysses J. et al., Prediction of the Apnea-Hypopnea Index From Overnight Pulse Oximetry, Chest the Cardiopulmonary and Critical Care Journal, 2003; vol. 124; pp. 1694-1701, Northbrook, IL, USA.

Manley,G.T.; Cerebral Oxygenation During Hemorrhagic Shock: Perils of Hyperventilation and the Therapeutic Potential of Hypoventilation, *J Trauma*: 2000; 48: 1025-1032.

Marin, José M., et al., Obstructive Sleep Apnea and Acute Myocardial Infarction: Clinical Implications of the Association, Sleep, vol. 21, No. 8, 1998, pp. 809-815.

Marin, Jose M., et al., Long-Term Cardiovascular Outcomes in Men with Obstructive sleep apnoea-hypopnoea with or without treatment with continuous positive airway pressure: an observational study, The Lancet, vol. 365, Issue 9464, Mar. 19, 2005-Mar. 25, 2005, pp. 1046-1053.

Mayer, Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.

McDannold, M. D., et al., Night-to-Night variability in Optimal CPAP Pressures Using Auto CPAP Titration in a Single Patient, Sleep Research No. 23, 1994, p. 453 (Abstract).

McEvoy, R. D., et al., Ventilatory responses to sustained eucapnic hypoxia in healthy males during wakefulness and NREM sleep, Sleep, vol. 20, No. 11, Nov. 1997, pp. 1008-1011 (Abstract).

McGregor, Christine D. et al., Performance of Pulse Oximeter Technologies in a Pediatric Sleep Lab Setting, OF-901-191, dated Nov. 2, 2001, Abstract.

McNicholas, W. T., et al., Diagnostic Criteria for the Sleep Apnoea Syndrome: Time for Consensus?, European Respiratory Journal, vol. 9, pp. 634-635, 1996, United Kingdom.

Mehra, Reena, et al., Association of Nocturnal Arrhythmias with Sleep-Disordered Breathing: The Sleep Heart Health Study, AJRCCM Articles in Press, Published Jan. 19, 2006, as doi: 10.1164/rccm.200509-1442OC, Copyright 2006 by the American Thoracic Society.

Mehta, Y. et al., Obstructive sleep apnea syndrome: anesthetic implications in the cardiac surgical patient, Journal Cardiothorac Vasc Anesth, Aug. 2000, vol. 14, No. 4, pp. 449-453 (Abstract).

Mendelson, W. B., et al., Effects of Hemodialysis on Sleep Apnea Syndrome in End-Stage Renal Disease, Clinical Nephrology, vol. 33, No. 5, 1990, pp. 247-251.

Middlekoop, Huub, et al., The Value of Nocturnal Motor Activity Monitoring as a Screening Tool for Obstructive Sleep Apnoea, Letter to the Editor, Journal Sleep Res., 1996, vol. 5, pp. 66-67.

Miles, L. E., et al., Development and Application of Automatic Nasal CPAP Calibration Procedures for Use in the Unsupervised Home Environment, Sleep, vol. 16, pp. S118-S119, 1993 American Sleep Disorders Association and Sleep Research Society.

Miles, Laughton E., Optimization of Nasal-CPAP Airflow Pressure by Use of Home Oximetry Recordings, Clinical Monitoring Center, Palo Alto, California, USA, Sleep Research, p. 568, 1987, Abstract.

Millard, R. K., Inductive plethysmography components analysis and improved non-invasive postoperative apnoea monitoring, Physiol Meas, May 1999, vol. 20, No. 2, pp. 175-186, United Kingdom (Abstract).

Mitler, Merrill M., et al., Narcolepsy and Its Treatment With Stimulants, ASDA Standards of Practice, Sleep, vol. 17, No. 4, pp. 352-371, 1994, American Sleep Disorders Association and Sleep Research Society.

Miyamura, Miharu, et al., $CO_2$ Dissociation Curves of Oxygenated Whole Blood Obtained at Rest and in Exercise, European Journal Applied Physiology, vol. 39, pp. 37-45, 1978, European Journal of Applied Physiology and Occupation Physiology.

Moller, J.T. et al.; *Hypoxaemia is Reduced by Pulse Oximetry Monitoring in the Operating Theatre and in the Recovery Room*; British Journal of Anaesthesia; 1992; vol. 68; pp. 146-150.

Moller, Jakob T. et al.; *Randomized Evaluation of Pulse Oximetry in 20,802 Pateints: I*; Anesthesiology, vol. 78, No. 3; Mar. 1993; pp. 436-444; US.

Moller, Jakob T. et al.; *Randomized Evaluation of Pulse Oximetry in 20,802 Patients: II*; Anesthesiology, vol. 78, No. 3; Mar. 1993; pp. 445-453; US.

Morelot-Panzini, Capucine et al., Simplified Method to Measure Respiratory-Related Changes in Arterial Pulse Pressure in Patients Receiving Mechanical Ventilation, Chest 2003, vol. 124, pp. 665-670, Northbrook, IL, USA.

Muller, Nestor L., et al., Mechanism of Hemoglobin Desaturation During Rapid-Eye-Movement Sleep in Normal Subjects and in Patients with Cystic Fibrosis, American Review of Respiratory Disease, vol. 121, 1980, pp. 463-469.

Murray, Carol B. et al.; *Making the most of pulse oximetry*; Contemporary Pediatrics; Jul. 1995; pp. 45-62.

Myatt, H. M., et al., Snoring—a simple surgical solution, Clin. Otolaryngol., 1996, vol. 21, pp. 419-424, Publisher: Blackwell Science Ltd.

Narkiewicz, Krzysztof, et al., Altered Cardiovascular Variability in Obstructive Sleep Apnea, Copyright 1998, American Heart Association, Inc., Iowa City, Iowa, USA, pp. 1071-1077, Published Sep. 15, 1998.

Naughton, Matthew T., et al., Sleep Apnea in Congestive Heart Failure, Clinics in Chest Medicine, vol. 19, No. 1, Mar. 1998, pp. 99-113.

Naughton, Matthew T., Cycling Sleep Apnea, The Balance of Compensated and Decompensated Breathing, American Journal of Respiratory and Critical Care Medicine, vol. 168, 2003, Editorials, pp. 624-625.

Neuman, Michael R.; *Pulse Oximetry: Physical Principles, Technical Relization and Present Limitations*; Adv Exp Med Biol 1987;220; pp. 135-144.

Neumann, Cristina et al., Nocturnal oxygen desaturation in diabetic patients with severe autonomic neuropathy, Diabetes Research and Clinical Practice, Publisher: Elsevier Science Ireland Ltd, vol. 28, 1995, pp. 97-102.

Netzer, Nikolaus, et al., Overnight Pulse Oximetry for Sleep-Disordered Breathing in Adults, A Review, Chest, vol. 120, #2, Aug. 2001, pp. 625-633, Northbrook, IL, USA.

Nobili, L. et al., Morning increase of whole blood viscosity in obstructive sleep apnea syndrome, Clinical Hemorheol Microcirc, 2000, vol. 22, No. 1, pp. 21-27 (Abstract).

Noda, A., et al., Daytime sleepiness and automobile accidents in patients with obstructive sleep apnea syndrome, Psychiatry & Clinical Neurosciences, vol. 52, No. 2, pp. 221-222, Apr. 1988 (Abstract).

Noda, Akiko, et al., Circadian Rhythm of Autonomic Activity in Patients with Obstructive Sleep Apnea Syndrome, Clinical Cardiology, vol. 21, pp. 271-276, 1998, Japan.

O'Donovan, Richard et al.; *Acid-Base Disturbances in Cardiogenic Polmonart Edema*; Nephron; 1991; 57; pp. 416-420.

Ogan, O. U., et al., Anesthetic safety always an issue with obstructive sleep apnea, Journal Clin Monit Comput, Jan. 1998, vol. 14, No. 1, pp. 69-70 (Abstract).

Ogretmenoglu, O., et al., Body fat composition: a predictive factor for obstructive sleep apnea, Laryngoscope, Aug. 2005, vol. 115, No. 8, pp. 1493-1498 (Abstract).

Ohga, Eijiro, et al., Increased Levels of Circulating ICAM-1, VCAM-1, and L-selectin in obstructive sleep apnea syndrome, Address for reprint requests and other correspondence: T. Nagase, Dept. of Geriatric Medicine, Faculty of Medicine, Univ. of Tokyo, 7-3-1, Hongo, Bunkyo-Ku, Tokyo 113, Japan, Received Nov. 13, 1998, accepted in final form Mar. 9, 1999.

Olson, L. G., et al., Prediction of Sleep-disordered breathing by unattended overnight oximetry, Journal Sleep Res., 1999, vol. 8, pp. 51-55, European Sleep Research Society.

Olson, Leslie G., et al., Chapter 10, A Biomechanical View of Upper Airway Function, pp. 359-389, 1988, Publisher, Marcel Dekker, Inc., New York—Basel, Book: Respiratory Function of the Upper Airway.

Ostermeier, A. M. et al., Three sudden postoperative respiratory arrests associated with epidural opioids in patients with sleep apnea, Anasth Analg., Aug. 1997, vol. 85, No. 2, pp. 452-460.

Owen, G. O., et al., Overnight Pulse Oximetry in Normal Children and in Children Undergoing Adenotonsillecomy, Clinical Otolaryngology, 1996 vol. 21, pp. 59-65, Blackwell Science Ltd.

Owen, G. O., et al., Overnight Pulse Oximetry in Snoring and Non-Snoring Children, Clinical Otolaryngology, 1995, vol. 20, pp. 402-406, Blackwell Science Ltd.

OxiScan, AirSep Corporation, 800/874-0202, Oxiscan Sample Report/Explanation and the Delta Sleep Apnea Index, OxiScan Sample Report, vol. 1, Rev. 01, Nov. 1997.

Pae, E. K., et al., Intermittent hypoxia damages cerebellar cortex and deep nuclei, Neurosci Lett., Feb. 28, 2005, vol. 375, No. 2, pp. 123-128 (Abstract).

Partinen, Markku, et al., Daytime Sleepiness and Vascular Morbidity at Seven-Year Follow-up in Obstructive Sleep Apnea Patients, Chest, vol. 97, No. 1, Jan. 1990, pp. 27-32.

Patil, Ramesh S. et al., Application of an Artificial Intelligence Program to Therapy of High-Risk Surgical Patients, New Horizons, vol. 4, No. 4, pp. 541-550.

Payne, J. P., Apnoeic Oxygenation in Anaesthetised Man, Acta Anaesth. Scandinav., 1962, vol. 6, pp. 129-142.

Peker, Y., et al., An independent association between obstructive sleep apnoea and coronary artery disease, European Respiratory Journal, 1999, vol. 14, No. 1, pp. 179-184 (Abstract).

Peker, Y., et al., Reduced hospitalization with cardiovascular and pulmonary disease in obstructive sleep apnea patients on nasal CPAP treatment, Sleep, 1997, vol. 20, No. 8, pp. 45-53 (Abstract).

Peled, N., et al., Nocturnal ischemic events in patients with obstructive sleep apnea syndrome and ischemic heart disease: effects of continuous positive air pressure treatment, Journal American Coll Cardiology, Nov. 1999, vol. 15, p. 34 (Abstract).

Pelttari, Lisa H., et al., Little Effect of Ordinary Antihypertensive Therapy on Nocturnal High Blood Pressure in Patients with Sleep Disordered Breathing, American Journal of Hypertension, 1998, vol. 11, No. 3, Part 1, pp. 272-279.

Penzel, T., et al., Systematic Comparison of Different Algorithms for Apnoea Detection Based on Electrocardiogram Recordings, Medical & Biological Engineering and Computing 2002, vol. 40, pp. 402-407.

Pepin et al., Does Oximetry contribute to the Detection of Apneic Events? Mathematical. Processing of the $SaO_2$ Signal, Chest, May 1991; 99: 1151-1157.

Peppard, Paul E., et al., Prospective Study of the Association Between Sleep-Disordered Breathing and Hypertension, May 11, 2000, vol. 342, No. 19, pp. 1378-1384.

Peters, John P. Jr., et al., Studies of the Carbon Dioxide Absorption Curve of Human Blood, Book: The Journal of Biological Chemistry, pp. 709-716, Received for publication, Feb. 7, 1923.

Peters, John P. Jr., et al., The Carbon Dioxide Absorption Curve and Carbon Dioxide Tension of the Blood of Normal Resting Individuals, Book: Carbon Dioxide Absorption Curve, pp. 489-547, Received for publication, Dec. 2, 1920 (missing pp. 490, 491, 538-541).

Phillips, Barbara A., et al., Catching Up on Sleep, The National Sleep Disorders Research Plan, Editorial, Chest, vol. 110, No. 5, Nov. 1996, pp. 1132-1133.

Phillips, Susan, et al., Obstructive Sleep Apnoea: Diagnosis and Management, Nursing Standard, vol. 11, No. 17, pp. 43-46, 1997.

Phillipson, Eliot A., Sleep Apnea—A Major Public Health Problem, Editorials, The New England Journal of Medicine, Editorials, vol. 328, No. 17, pp. 1271-1273, Apr. 29, 1993.

Plastiras, James, Sleep disorders create need for more sleep labs, Capital District Business Review, Mar. 9, 1998.

Poets, C. F., et al., Arterial oxygen saturation and breathing movements during the first year of life, Journal Developmental Physiology, Jun. 1991, vol. 15, No. 6, pp. 341-345 (Abstract).

Poets, C. F., et al., Home monitoring of transcutaneous oxygen tension in the early detection of hypoxaemia in infants and young children, Arch Dis Child, Jun. 1991, vol. 66, No. 6, pp. 676-682 (Abstract).

Poets, C. F., et al., Oxygen saturation and breathing patterns in infancy. 2: Preterm infants at discharge from special care, Arch Dis Child, May 1991, vol. 66, No. 5, pp. 574-578 (Abstract).

Poets, C. F., et al., Patterns of oxygenation during periodic breathing in preterm infants, Early Human Development, Jul. 1991, vol. 26, No. 1, pp. 1-12 (Abstract).

Poets, C. F., Apparent life-threatening events and sudden infant death on a monitor, Paediatr Respiratory Review, 2004, Suppl. A, pp. S383-S386 (Abstract).

Pradhan, Pratik S., et al., Screening for Obstructive Sleep Apnea in Patients Presenting for Snoring Surgery, Laryngoscope, vol. 106, Nov. 1996, pp. 1393-1397.

Principe-Rodriguez, K., et al., Sleep symptoms and clinical markers of illness in patients with heart failure, Sleep Breath., Sep. 2005, vol. 9, No. 3, pp. 127-133 (Abstract).

Quinn, S. J., et al., The Differentiation of Snoring Mechanisms Using Sound Analysis, Clinical Otolaryngol., 1996, vol. 21, pp. 119-123, Publisher: Blackwell Science Ltd.

Randerath, Winfried J., et al., Autoadjusting CPAP Therapy Based on Impedance Efficacy, Compliance and Acceptance, American Journal Respiratory Critical Care Medicine, vol. 163, pp. 652-657, 2001, Internet address: www.atsjournals.org.

Rapoport, David M., et al., Reversal of the "Pickwickian Syndrome" by Long-Term Use of Nocturnal Nasal-Airway Pressure, The New England Journal of Medicine, Oct. 7, 1982, vol. 307, No. 15, pp. 931-933.

Rapoport, et al., CO2 Homeostasis During Periodic Breathing: Predictions From a Computer Model, The American Journal of Applied Physiological, 1993, vol. 75, Issue 5, pp. 2302-2309.

Rauscher et al., Computerized Detection of Respiratory Events During Sleep from Rapid Increases in Oxyhemoglobin Saturation, Lung, 1991; 169: 355-42.

Rauscher et al., Quantification of sleep-disordered breathing by computerized analysis of oximetry, heart rate, and snoring, Eur Respir J. Jun. 1991; 4: 655-659.

Rauscher, Helmuth, et al., Computerized Detection of Respiratory Events During Sleep from Rapid Increases in Oxyhemoglobin Saturation, Lung, 1991, vol. 169, pp. 335-342.

Redline, Susan, et al., Hypopnea, a Floating Metric: Implications for Prevalence, Morbidity Estimates, and Case Finding, Sleep, vol. 20, No. 12, pp. 1209-1217 (1997).

Redline, Susan, et al., Recognition and Consequences of Obstructive Sleep Apnea Hypopnea Syndrome, Sleep Disorders, Clinics in Chest Medicine, vol. 19, No. 1, Mar. 1998, Cleveland, Ohio, USA (Article and Abstract).

Reite, Martin, et al., The Use of Polysomnography in the Evaluation of Insomnia, An American Sleep Disorders Association Review, Sleep, vol. 18, No. 1, 1995, pp. 58-70, American Sleep Disorders Association and Sleep Research Society 1995.

Remmers, John E., et al., Nasal Airway Positive Pressure in Patients with Occlusive Sleep Apnea, Methods and Feasibility, American Review Respiratory Disorders, Dec. 1984, vol. 130, No. 6, pp. 1152-1155.

Rennotte, M. T., Epidural opioids and respiratory arrests, Anesth Analg., Aug. 1997, vol. 85, No. 2, pp. 452-460 (Abstract).

Resta, O., et al., Sleep-related breathing disorders in acute respiratory failure assisted by non-invasive ventilatory treatment: utility of portable polysomnographic system, Respir Medicine, Feb. 2000, vol. 94, No. 2, pp. 128-134 (Abstract).

Riley, Robert W., et al., Maxillofacial Surgery and Nasal CPAP, A Comparison of Treatment for Obstructive Sleep Apnea Syndrome, Chest, vol. 98, No. 6, Dec. 1990, pp. 1421-1425.

Riley, Robert W., et al., Maxillofacial Surgery and Obstructive Sleep Apnea: A Review of 80 Patients, Otolaryngology—Head and Neck Surgery, vol. 101, No. 3, Sep. 1989, pp. 353-361.

Riley, Robert W., et al., Maxillofacial Surgery and Obstructive Sleep Apnea Syndrome, Otolaryngologic Clinics of North America, vol. 23, No. 4, Aug. 1990, pp. 809-824.

Rosenberg, J., et al., Ventilatory Pattern and Associated Episodic Hypoxaemia in the Late Postoperative Period in the General Surgical Ward, Anaesthesia, 1999, vol. 54, pp. 323-328, Publisher: Blackwell Science Ltd.

Roux, Francoise, et al., Sleep-related Breathing Disorders and Cardiovascular Disease, The American Journal of Medicine, Apr. 1, 2000, vol. 108, pp. 396-400.

Ruchala, Joanna B., Chapter 13, Applications of Pulse Oximetry, Book: Design of Pulse Oximeters, pp. 214-236.

Ruhle, K. H., et al., Monitoring at Home, Lung, 1990, Suppl, pp. 927-932, Lung, Springer-Verlag, New York, Inc. 1990.

Rundell, O. H., et al., Polysomnography Methods and Interpretations, Sleep Apnea, Otolaryngologic Clinics of North America, vol. 23, No. 4, Aug. 1990, pp. 583-592.

Rusch, T. L., et al., Signal Processing Methods for Pulse Oximetry, Computers in Biology & Medicine, vol. 26, No. 2, pp. 143-159, Mar. 1996 (Abstract).

Ryan, C. Francis, et al., Mechanical Properties of the Velopharynx in Obese Patients with Obstructive Sleep Apnea, American Journal Respiratory Critical Care Medicine, 1996, vol. 154, pp. 806-812.

Ryan, Clodagh M., et al., Periodicity of Obstructive Sleep Apnea in Patients With and Without Heart Failure, Chest 2005; 127, pp. 536-542.

Saarelainen, Seppo, et al., Effect of Nasal CPAP Treatment on Plasma Volume, Aldosterone and 24-h Blood Pressure in Obstructive Sleep Apnoea, Journal Sleep Research, 1996, vol. 5, pp. 181-185.

Sadeh, Avi, et al., The Role of Actigraphy in the Evaluation of Sleep Disorders, An American Sleep Disorders Association and Sleep Research Society, Sleep, vol. 18, No. 4, pp. 288-302.

Sadrmoori, Bijan, Evaluation of Self Adjusting Nasal CPAP (DPAP) in the Treatment of Adult Obstructive Sleep Apnea, Sleep Research No. 23, 1994, p. 386 (Abstract).

Saito, Toshiyuki, et al., Sleep Apnea in Patients with Acute Myocardial Infarction, Critical Care Medicine, vol. 19, No. 7, pp. 938-941, Printed in USA, Copyright 1991 by Williams and Wilkins.

Sajkov, Dimitar, et al., Daytime Pulmonary Hemodynamics in Patients with Obstructive Sleep Apnea without Lung Disease, American Journal Respiratory Critical Care Medicine, 1999, vol. 159, pp. 1518-1526.

Salmi, et al., Evaluation of Automatic Analysis of SCSB, Airflow and Oxygen Saturation Signals in Patients with Sleep Related Apneas, Chest, 1989; 96: 255-61.

Sanders, Mark H., et al., Obstructive Sleep Apnea Treated by Independently Adjusted Inspiratory and Expiratory Positive Airway Pressures via Nasal Mask, Physiologic and Clinical Implications, Chest, vol. 98, No. 2, Aug. 1990, pp. 317-324.

Sanders, Mark H., Nasal CPAP Effect on Patterns of Sleep Apnea, Chest, vol. 86, No. 6, Dec. 1984, pp. 839-844.

Sangal, R. Bart et al., P300 Latency: Abnormal in Sleep Apnea with Somnolence and Idiopathic Hypersomnia, but Normal in Narcolepsy, Clinical Electroencephalography, 1995, vol. 26, No. 3, pp. 146-153, Troy, Michigan, USA.

Sanna, A., et al., Apport de la Polysomnographie à la mise au point des maladies atteints d'une bronchopneumopathie chronique obstructive (BPCO), Travail Original, Rev. Mèd. Brux., vol. 12, pp. 315-320, 1991, Belgium.

Sanner, B. M., et al., Sleep-related respiration disorders: their relevance in intensive care medicine, [Article in German], Dtsch Med Wochenschr, Mar. 1999, vol. 12, p. 124 (Abstract).

Sarodia, B.D. et al. Prevalence of obstructive sleep apnea in patients admitted to the intensive care unit with cardiovascular events, Sleep Research, 1996, vol. 25, pp. 356.

Schafer, H., et al., Cardiovascular morbidity in patients with obstructive sleep apnea in relation to the severity of respiratory disorder, Dtsch Med Wochenschr, 1998, vol. 123, No. 39, pp. 1127-1133 (Abstract).

Schafer, H., et al., Pulmonary Haemodynamics in Obstructive Sleep Apnoea: Time Course and Associated Factors, European Respiratory Journal, 1998, vol. 12, pp. 679-684, Printed in United Kingdom.

Schagatay, E., et al., Diving Response and Apneic Time in Humans, Undersea Hyper Med., 1998, vol. 25, No. 1, pp. 13-19, Copyright 1988 Underseas and Hyperbaric Medical Society, Inc.

Scharf, Martin B., et al., Cyclic Alternating Pattern Sequences in Non-Apneic Snorers With and Without Nasal Dilation, ENT-Ear, Nose & Throat Journal, Sep. 1996, vol. 75, No. 9, pp. 617-619.

Scharf, Steven M., et al., Cardiovascular Effects of Periodic Occlusions of the Upper Airways in Dogs, American Review of Respiratory Disease, pp. 321-329.

Scheers, N. J., et al., Sudden Infant Death With External Airways Covered, Case-Comparison Study of 206 Deaths in the United States, Arch Pediatric Adolescent Medicine, 1998, vol. 152, pp. 540-547.

Schmidt-Notwara, Wolfgang, et al., Oral Appliances for the Treatment of Snoring and Obstructive Sleep Apnea: A Review, An American Sleep Disorders Association Review, Sleep, vol. 18, No. 6, pp. 501-510, 1995, American Sleep Disorders Association and Sleep Research Society.

Schnader, Jeff, Increase of Pulmonary Artery Occlusion Pressure During Upper Airway Obstruction in Sleep Apnea, Case Reports, Critical Care Medicine, 1996, vol. 24, No. 2, pp. 354-358.

Schnapp, Lynn M., et al., Pulse Oximetry Uses and Abuses, Critical Care, Chest, vol. 98, No. 5, Nov. 1990, pp. 1244-1250.

Schneider, H., et al., Neural and local effects of hypoxia on cardiovascular responses to obstructive apnea, Journal Appl Physiol., Mar. 2000, vol. 88, No. 3, pp. 1093-1092 (Abstract).

Schoenberg, R., et al., Making ICU Alarms Meaningful: A Comparison of Traditional vs. Trend-Based Algorithms, AMIA 1999, Annual Symposium (Abstract).

Schwab, Richard J., et al., Upper Airway and Soft Tissue Structural Changes Induced by CPAP in Normal Subjects, American Journal Respiratory Critical Care Medicine, 1996, vol. 154, pp. 1106-1116.

Senn, Oliver et al., Monitoring Carbon Dioxide Tension and Arterial Oxygen Saturation by a Single Earlobe Sensor in Patients With Critical Illness or Sleep Apnea, Chest 2005, vol. 128, pp. 1291-1296, Northbrook, IL, USA.

Series et al., Utility of Nocturnal Home Oximetry for Case Finding in Patients with Suspected Sleep apnea Hypopnea Syndrome, Sep. 15, 1993, Annals of Internal Medicine, col. 119, p. 449-453.

Series, et al., Influence of Continuous Positive Airways Pressure on Sleep Apnea-Related Desaturation in Sleep Apnea Patients, Lung, 1992; 170: 281-290.

Series, Frederic, et al., Prospective Evaluation of Nocturnal Oximetry for Detection of Sleep-Related Breathing Disturbances in Patients With Chronic Heart Failure, Chest 2005, vol. 127, pp. 1507-1514, Northbrook, IL, USA.

Severinghaus, John W., et al., Recent Developments in Pulse Oximetry, Anesthesiology, vol. 76, pp. 1018-1038, 1992.

Shamir, M. et al., Pulse oximetry plethsymographic waveform during changes in blood volume, British Journal of Anaesthesia, vol. 82(2), pp. 178-181, 1999, Great Britain.

Shepard, J., Gas Exchange and Hemodynamics During Sleep, Medical Clinics of North America, vol. 69, No. 6, Nov. 1985, pp. 1243-1265.

Shephard, John W. Jr., et al., Relationship of Ventricular Ectopy to Oxyhemoglobin Desaturation in Patients with Obstructive Sleep Apnea, Chest, vol. 88, No. 3, Sep. 1985, pp. 335-340, Northbrook, IL, USA.

Shephard, John W., Jr., et al., Uvulopalatopharyngoplasty for Treatment of Obstructive Sleep Apnea, Mayo Clinic Proceedings, vol. 65, pp. 1260-1267, 1990.

Sher, Aaron E., et al., The Efficacy of Surgical Modifications of the Upper Airway in Adults With Obstructive Sleep Apnea Syndrome, An American Sleep Disorders Association Review, Sleep, vol. 19, No. 2, pp. 156-177, Nov. 1995.

Shinohara, E., et al., Visceral Fat Accumulation as an Important Risk Factor for Obstructive Sleep Apnoea Syndrome in Obese Subjects, Journal of Internal Medicine, vol. 241, pp. 11-18, Publisher: Blackwell Science Ltd., 1997.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High-Risk Surgical Patients, Archives of Surgery, vol. 131, No. 7, Jul. 1996, pp. 732-737.

Shoemaker, W. C. et al., Prediction of Outcome and Severity of Illness by Analysis of the Frequency Distributions of Cardiorespiratory Variables, Critical Care Medicine, vol. 5, No. 2, Mar.-Apr. 1977, pp. 82-88.

Shoemaker, W. C. et al., Sequence of Physiologic Patterns in Surgical Septic Shock, Critical Care Medicine, Dec. 21, 1993 (12): pp. 1821.

Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.

Shoemaker, W. C., Early Physiologic Patterns in Acurate Illness and Accidents: Toward A Concept of Circulatory Dysfunction and Shock Based on Invasive and Noninvasive Hemodynamic Monitoring, New Horizons, Nov. 1996, vol. 4, No. 4, pp. 395-412.

Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.

Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.

Siggaard-Andersen O. et al.; *The Bohr Effect and the Haldane Effect*; Scand J Clin Lab Invest; vol. 3 (1); 1973; pp. 1-8.

Silverberg, D. S., et al., Essential and Secondary Hypertension and Sleep-Disordered Breathing: A Unifying Hypothesis, Journal of Human Hypertension, 1996, vol. 10, pp. 353-363.

Silverberg, D., et al., Sleep apnoea and hypertension. Active approach to detection of obstructive sleep apnoea is imperative, BMJ, Jul. 2000, vol. 22, pp. 321 (Abstract).

Silverberg, Donald, The Joint National Committee on Prevention, Detection, Evaluation, and Treatment of High Blood Pressure and Obstructive Sleep Apnea: Let Their Silence Not Be Matched by the Silence of the Ordinary Physician, Arch Intern Med., Jun. 8, 1998, vol. 158, pp. 1272-1273.

Simmons, Richard L. et al.; *The Role of the Central Nervous System in Septic Shock: II. Hemodynamic, Respiratory and Metabolic Effects of Intracisternal or Intraventricular Endotoxin*; Annals of Surgery; Feb. 1968; pp. 158-167.

Sin, D. D., et al., Effects of continuous positive airway pressure on cardiovascular outcomes in heart failure patients with and without Cheyne-Stokes respiration, Circulation, Jul. 2000, vol. 102, No. 1, pp. 61-66 (Abstract).

Sinex, James E.; *Pulse Oximetry: Principles and Limitations*; American Journal of Emergency Medicine; vol. 17, No. 1; Jan. 1999; pp. 59-66.

Skjodt, N. M., et al., Screening for hypothyroidism in sleep apnea, American Journal of Respiratory & Critical Care Medicine, vol. 160, No. 2, pp. 732-735, Aug. 1999 (Abstract).

Slutsky et al., Quantification of Oxygen Saturation During Episodic Hypoxemia, American Review of Respiratory Disease, 1980; 121:893-895.

Smith, Philip E. M., et al., Hypoxemia During Sleep in Duchenne Muscular Dystrophy, American Review Respiratory Disorders, 1988, vol. 137, pp. 884-888.

Smyth, Edward, et al., Apneic Oxygenation Associated with Patient-Controlled Analgesia, Journal of Clinical Anesthesia, vol. 10, pp. 499-501, 1998, Publisher: Elsevier Science, Inc., New York, NY, USA.

Soto, F., Cardiovascular manifestations of obstructive sleep apnea. Effects of the treatment, Rev Med Chil., [Article in Spanish], Sep. 1998, vol. 126, No. 9, pp. 1112-1116 (Abstract).

Soubani, Ayman O.; *Noninvasive Monitoring of Oxygen and Carbon Dioxide*; American Journal of Emergency Medicine; vol. 19, No. 2; Mar. 2001; pp. 141-146.

Spector, Rosanne, Low-tech Screening for high-risk breathing disorder, http://healthlink.stanford.edu/healthlink/news2/lowtech.thml, Copyright 1996 Stanford University Medical Center News Bureau.

Staniforth, A. D., et al., Nocturnal desaturation in patients with stable heart failure, Heart, Apr. 1998, vol. 79, No. 4, pp. 394-399, United Kingdom.

Stebbens, V. A., Oxygen saturation and breathing patterns in infancy. 1: Full term infants in the second month of life, Arch Dis Child, May 1991, vol. 66, No. 5, pp. 569-573 (Abstract).

Stegman, S. S., et al., Asymptomatic bradyarrhythmias as a marker for sleep apnea: appropriate recognition and treatment may reduce the need for pacemaker therapy, Pacing Clin Electrophysiol, Jun. 1996, vol. 19, No. 6, pp. 899-904 (Abstract).

Stradling, J. R., et al., Automatic Nasal Continuous Positive Airway Pressure Titration in the Laboratory: Patient Outcomes, Thorax, 1997, vol. 52, pp. 72-75.

Stradling, J. R., et al., Predictors and Prevalence of Obstructive Sleep Apnoea and Snoring in 1001 Middle Aged Men, Thorax, 1991, vol. 46, pp. 85-90.

Stradling, John R., et al., Relation between systemic hypertension and sleep hypoxaemia or snoring: analysis in 748 men drawn from general practice, BMJ, vol. 300, Jan. 13, 1990, pp. 75-78.

Strohl et al., Oxygen Saturation During Breath Holding and During Apneas in Sleep, Chest, Feb. 1984: 85, No. 1; 181-186.

Strohl, Kingman P., Consequences of Sleep-Disordered Breathing, Respiratory Care, Apr. 1998, vol. 43, No. 4, pp. 277-282.

Strohl, Kingman P., et al., Physiologic Basis of Therapy for Sleep Apnea, State of Art: Physiologic Basis of Therapy for Sleep Apnea, pp. 791-802.

Sullivan, Colin E., et al., Reversal of Obstructive Sleep Apnoea by Continuous Positive Airway Pressure applied through the Nares, The Lancet, Apr. 18, 1981, pp. 862, 865.

Sullivan, Mary Anna et al., PCA Update, Unexpected Deaths of Patients Receiving Patient-Controlled Analgesia, Nov. 2001.

Svanborg, et al., A Limited diagnostic Investigation for Obstructive Sleep Apnea Syndrome: Oximetry and Static Charge Sensitive Bed, Chest, 1990; 98: 1341-45.

Svatikova, A., et al., Plasma brain natriuretic peptide in obstructive sleep apnea, American Journal Cardiology, Aug. 15, 2004, vol. 94, No. 4, pp. 529-532 (Abstract).

Szaboova, E., et al., Obstructive Sleep Apnea as a Cause of Dysrhythmia in Sudden Cardiac Death, Bratisl Lek Listy, Jul.-Aug. 1997, vol. 98, No. 7-8, pp. 448-453 (Abstract).

Tan and T. H. Koh, Evaluation of Obstructive Sleep Apnea in Singapore Using Computerized Polygraphic Monitoring, Annals Academy of Medicine, Mar. 1991, vol. 20 No. 2, pp. 196-200.

Tanchaiswad, Waran, Is Sudden Unexplained Nocturnal Death a Breathing Disorder?, Review Article, Psychiatry and Clinical Neurosciences, 1995, vol. 49, pp. 111-114.

Tang, et al.; *Perepheral neural modulation of endotoxin-induced hyperventilation*; Critical Care Medicine; vol. 26, Issue 9; Sep. 1998, pp. 1558-1563.

Tanigawa, T., et al., Screening for sleep-disordered breathing at workplaces, Ind. Health, Jan. 2005, vol. 43, No. 1, pp. 53-57 (Abstract).

Tatevossian, Raymond G., et al., Noninvasive Hemodynamic Monitoring for Early Warning of Adult Respiratory Distress Syndrome in Trauma Patients, Journal of Critical Care, vol. 15, No. 4 (Dec.), 2000, pp. 151-159.

Tatevossian, Raymond G., et al., Transcutaneous oxygen and C02 as early warning of tissue hypoxia and hemodynamic shock in critically ill emergency patients ; *Critical Care Med*.; vol. 28, No. 7; pp. 2248-2253 (2000).

Teramoto, S., et al., Does the altered cardiovascular variability associated with obstructive sleep apnea contribute to development of cardiovascular disease in patients with obstructive sleep apnea syndrome?, Circulation, Dec. 21, 1999, vol. 100, No. 25, pp. e136-e137 (Abstract).

Teschler, H., et al., Influence of Moderate Alcohol Consumption on Obstructive Sleep Apnoea with and without AutoSet™ Nasal CPAP Therapy, European Respiratory Journal, 1996, vol. 9, pp. 2371-2377, Printed in United Kingdom.

Teschler, Helmut, et al., Automated Continuous Positive Airway Pressure Titration for Obstructive Sleep Apnea Syndrome, American Journal Respiratory Critical Care Medicine, vol. 154, pp. 734-740, 1996.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy, Michael J., The Clinical Use of the Multiple Sleep Latency Test, Report From the American sleep Disorders Association, Sleep, vol. 15, No. 3, 1992, pp. 268-276, American Sleep Disorders Association and Sleep Research Society.

Thorpy, Michael, et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377 (1994).

Thorpy, Michael, et al., Practice Parameters for the Treatment of Obstructive Sleep Apnea in Adults: The Efficacy of Surgical Modifications of the Upper Airway, An American Sleep Disorders Association Review, Sleep, vol. 19, No. 2, pp. 152-155, 1996, American Sleep Disorders Association and Sleep Research Society.

Thorpy, Michael, et al., Practice Parameters for the Treatment of Snoring and Obstructive Sleep Apnea with Oral Appliances, An American Sleep Disorders Association and Sleep Research Society, Sleep, vol. 18, No. 6, pp. 511-513, 1995.

Thorpy, Michael, et al., Practice Parameters for the Use of Actigraphy in the Clinical Assessment of Sleep Disorders, An American Sleep Disorders Association Report, Sleep, vol. 18, No. 4, pp. 285-287, 1995 American Sleep Disorders Association and Sleep Research Society.

Thorpy, Michael, et al., Practice Parameters for the Use of Laser-assisted Uvulopalatoplasty, An American Sleep Disorders Association and Sleep Research Society, Sleep, vol. 17, No. 8, pp. 744-748, 1994.

Thorpy, Michael, et al., Practice Parameters for the Use of Polysomnography in the Evaluation of Insomnia, An American Sleep Disorders Association Report, Sleep, vol. 18, No. 1, pp. 55-57, 1995 American Sleep Disorders Association and Sleep Research Society.

Timms Et Al., Oxygen Saturation by Oximetry: analysis by Microcomputer, Journal of Polysomographic Technology, Spring 1988: 13-21.

Timms, et al., and PROFOX Associates, Inc., Profox for the Bedside, Version 8SP Nov. 1992, Programs for Oximetry [IBM], User's Manual, Nov. 1992, 20 total pages.

Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262 (Abstract).

Tkacova, R., et al., Effects of continuous positive airway pressure on obstructive sleep apnea and left ventricular afterload in patients with heart failure, Circulation, 1998, vol. 98, No. 21, pp. 2269-2275 (Abstract).

Tobert, Daren G., et al., Laboratory Medicine and Pathology, New Directions for Pulse Oximetry in Sleep Disorders, Mayo Clinic Proceedings, 1995, vol. 70, pp. 591, Rochester, Minnesota, USA.

Tobin, Martin J., et al., Breathing Abnormalities During Sleep, Arch Intern Med, vol. 143, Jun. 1983, pp. 1221-1228.

Trang, H., et al., [B20] [Poster: 904] Masimo SetR Pulse Oximetry Improves Detection of Sleep Apnea-Related Hypoxemia, Nov. 2, 2001, C:/Masimo/Biblio, p. 1 of 1.

Tremel, F., et al., High prevalence and persistence of sleep apnoea in patients referred for acute left ventricular failure and medically treated over 2 months, European Heart Journal, Aug. 1999, vol. 20, No. 16, pp. 120-129.

Trinder, J., et al., Pathiophysiological interactions of ventilation, arousals, and blood pressure oscillations during Cheyne-Stokes respiration in patients with heart failure, American Journal Respiratory Critical Care Medicine, Sep. 2000, vol. 162, No. 3 Pt. 1, pp. 808-813 (Abstract).

Trupp, R. J., et al., Prevalence of sleep disordered breathing in a heart failure program, Congestive Heart Failure, Sep.-Oct. 2004, vol. 10, No. 5, pp. 217-220 (Abstract).

Trupp, R. J., The heart of sleep: sleep-disordered breathing and heart failure, Journal Cardiovascular Nursing, Nov.-Dec. 2004, vol. 19, No. 6 Suppl, S67-74 (Abstract).

Ullmer, E., et al., Cheyne-stokes respiration or obstructive sleep apnoea: patterns of desaturation, Respiration, 2000, vol. 67, No. 2, p. 203 (Abstract).

VanBoxem, T. J., et al., Prevalence and severity of sleep disordered breathing in a group of morbidly obese patients, Netherlands Journal of Medicine, vol. 54, No. 5, pp. 202-206, May 1999 (Abstract).

VanSlyke, Donald D., et al., Studies of Gas and Electrolyte Equilibria in Blood, pp. 781-798, Journal Biol. Chem., Oct. 1928, vol. 79, No. 2.

Vázquez, Juan-Carlos, et al.; "Automated Analysis of Digital Oximetry in the Diagnosis of Obstructive Sleep Apnoea,"; *Thorax*, vol. 55, pp. 302-307; 2000.

Verbraecken, J., et al., Chronic $CO_2$ Drive in Patients with Obstructive Sleep Apnea and Effect of CPAP, Respiration Physiology, vol. 101, pp. 279-287, 1995, Publisher: Elsevier.

Vgontzas, Alexandros N., et al., Obesity Without Sleep Apnea Is Associated with Daytime Sleepiness, Arch Intern Med., Jun. 22, 1998, vol. 158, pp. 1333-1337.

Vidhani, K., et al., Obstructive sleep apnoea syndrome: is this an overlooked cause of desaturation in the immediate postoperative period?, British Journal Anaesth, Apr. 1997, vol. 78, No. 4, pp. 442-443 (Abstract).

Visser, B.F., Pulmonary Diffusion of Carbon Dioxide, Med. Biol. vol. 5, pp. 155-166, Issue 2, Oct. 1960.

Waldhorn, Richard E., Surgical Treatment of Obstructive Sleep Apnea, Is Mandibular Surgery an Advance?, Chest, 1998, vol. 6, Dec. 1990, pp. 1315-1316.

Walker, Regina Paloyan, et al., Uvulopalatopharyngoplasty Versus Laser-Assisted Uvulopalatoplasty for the Treatment of Obstructive Sleep Apnea, Laryngoscope, vol. 107, Jan. 1997, pp. 76-82.

Weber, W., et al., Low-Perfusion Resistant Pulse Oximetry, Abstract Only, Journal of Clinical Monitoring, vol. II, No. 4, Jul. 1995, p. 284.

Weiss, et al., "Computer Assisted Physiologic Monitoring and Stability Assessment in Vascular Surgical Patients Undergoing General Anesthesia—Preliminary Data," Journal of Clinical Monitoring and Computing, 16:107-113, 2000.

Weiss, J. Woodrow, et al., Cardiovascular Morbidity in Obstructive Sleep Apnea, Progress in Cardiovascular Diseases, vol. 41, No. 5, Mar./Apr. 1999, pp. 367-376.

Wessendorft, T. E., et al., Sleep-disordered breathing among patients with first-ever stroke, Journal Neurology, Jan. 2000, vol. 247, No. 1, pp. 41-47 (Abstract only).

West, Peter, et al., Dynamic in Vivo Response Characteristics of Three Oximeters: Hewlett-Packard 47201A, Biox III, and Nellcor N-100, Sleep, vol. 10, No. 3, 1987, pp. 263-271, Raven Press, New York, USA.

Westesson, Per-Lennart, et al., Morbidity after temporomandibular joint arthrography is lower than after removal of lower third molars, Oral Surgery Oral Medical Oral Pathol., 1990, vol. 70, pp. 2-4.

Wheatley, J. R., et al., Mechanical properties of the upper airway, Curr Opin Pulm Medicine, Nov. 1998, vol. 4, No. 6, pp. 363-369 (Abstract).

White, D. P., et al., Assessment of Accuracy and Analysis Time of a Novel Device to Monitor Sleep and Breathing in the Home, Sleep, vol. 18, No. 2, Feb. 1995, pp. 115-26.

White, David P., Pathophysiology of Obstructive Sleep Apnoea, Sleep-Related Breathing Disorder—2, Thorax, 1995, vol. 50, pp. 797-804.

Whitelaw, William A., et al., Clinical Usefulness of Home Oximetry Compared with Polysomnography for Assessment of Sleep Apnea, American Journal Respiratory Critical Care Medicine, vol. 171, pp. 188-193, 2005, Internet address: www.atsjournals.org.

Whitman, R. A., et al., Comparison of the New Masimo SET V3 Technology with a Conventional Pulse Oximeter during Polysomnography, Sleep, 2001, vol. 24, pp. A412 (730.R).

Wiater, A., et al., Polysomnographic Standards for Infants and Children, Somnologie, vol. 4, pp. 39-42, 2000, Berlin—Wien.

Wieczorek, Paul M., et al., Obstructive Sleep Apnea Uncovered After High Spiral Anesthesia: A Case Report, Cardiothoracic Anesthesia, Respiration and Airway, Canadian Journal of Anesthesia, 2005, vol. 52, No. 7, pp. 761-764.

Wilhoit, Stephen C., et al., Comparison of Indices Used to Detect Hypoventilation during Sleep, Respiration, vol. 47, pp. 237-242, 1985.

Wilkins, Robert L., et al., EGAN'S Fundamentals of Respiratory Care, Analysis and Monitoring of Gas Exchange, Book, Eighth Edition, Chapter 16, Section III, Capnography/Capnometry During Mechanical Ventilation, pp. 383-389.

Wilkinson, M. H., et al., Effect of Venous Oxygenation on Arterial Desaturation Rate During Repetitive Apneas in Lambs, Respiration Physiology 101 (19950 321-331.

Williams, Adrian J., et al., Clinical Value of Polysomnography, The Lancet, vol. 339, May 2, 1992, p. 1113.

Williams, et al., Screening for Sleep Apnea Using Pulse Oximetry and a Clinical Score, Chest, 100/3, Sep. 1991; pp. 631-635.

Wright, John, et al., Health effects of obstructive sleep apnoea and the effectiveness of continuous positive airways pressure: a systematic review of the research evidence, BMJ, vol. 314, Mar. 22, 1997, pp. 851-860.

Wright, John, et al., Letters, Obstructive Sleep Apnoea, Authors' reply, bmj.com, Jun. 26, 2001.

Wynne, James W., et al., Disordered Breathing and Oxygen Desaturation During Sleep in Patients with Chronic Obstructive Lung Disease (COLD), The American Journal of Medicine, vol. 66, Apr. 1979, pp. 573-579.

Yamakage, M., et al., Changes in respiratory pattern and arterial blood gases during sedation with propofol or midazolam in spinal anesthesia, Journal Clinical Anesth, Aug. 1999, vol. 11, No. 5, pp. 375-379 (Abstract).

Yantis, M. A., Decreasing surgical risks for patients with obstructive sleep apnea, AORN Journal, Jul. 1998, vol. 68, No. 1, pp. 50-55 (Abstract).

Younes, Magdy, et al. Chemical Control Stability in Patients with Obstructive Sleep Apnea, American Journal Respiratory Critical Care Medicine, vol. 163, pp. 1181-1190, 2001.

Young, Terry, et al., The Gender Bias in Sleep Apnea Diagnosis, Are Women Missed Because They Have Different Symptoms?, Original Investigation, Arch Intern Medicine, vol. 156, Nov. 25, 1996, pp. 2445-2451.

Zafar, Subooha, et al., Choice of Oximeter Affects Apnea-Hypopnea Index, Chest, vol. 127/1, Jan. 2005, pp. 80-88, Clinical Investigations, www.chestjournal.org.

Zamarron, C. et al., Oximetry Spectral Analysis in the Diagnosis of Obstructive Sleep Apnoea, Clinical Science, 1999, vol. 97, pp. 467-473, Printed in Great Britain.

Zoccali, Carmine, et al., Nocturnal Hypoxemia, Night-Day Arterial Pressure Changes and Left Ventricular Geometry in Dialysis Patients, Kidney International, vol. 53, 1998, pp. 1078-1084, International Society of Nephrology.

Zucconi, M., et al., An unattended device for sleep-related breathing disorders: validation study in suspected obstructive sleep apnoea syndrome, European Respiratory Journal, 1996, vol. 9, pp. 1251-1256, Printed in United Kingdom.

Zou, Ding, et al., Obstructive Apneic Events Induce Alpha-Receptor Mediated Digital Vasoconstriction, Sleep, vol. 27, No. 3, 2004, pp. 485-489.

* cited by examiner

SYSTEM AND METHOD FOR DETECTING VENTILATORY INSTABILITY

BACKGROUND

The present disclosure relates generally to medical devices and methods and, more particularly, to an automated system and method for detecting events related to ventilatory instability, such as sleep apnea.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Sleep apnea is generally described as a sleep disorder that is characterized by episodes of paused breathing during sleep. These episodes of paused breathing may occur repeatedly throughout sleep, and each episode may last long enough to cause one or more breaths to be missed. Such episodes may be referred to as apneas. A typical definition of an apnea may include an interval between breaths of at least 10 seconds, with a neurological arousal and/or a blood oxygen desaturation of 3% or greater. The actual duration and severity of each apnea may substantially vary between multiple patients. Further, duration and severity of apneas may vary throughout a period of sleep for a single patient. Indeed, sleep apnea may have a wide range of severity. For example, sleep apnea may include mild snoring, which may be related to incomplete and inconsequential airway obstruction, or severe apneas, which may result in hypoxemia. Sleep apnea commonly results in excessive daytime sleepiness. Further, sleep apnea can hinder cognitive function during the day due to sporadic sleep during the night resulting from recurrent arousals associated with the sleep apnea.

Although sleep apnea commonly affects obese patients, it may occur in patients with any body type. Indeed, sleep apnea is fairly common and causes undesirable symptoms of excessive daytime sleepiness, morning headache, and decreasing ability to concentrate during the day. Thus, it is desirable to diagnose and treat sleep apnea. Traditionally, sleep apnea is diagnosed utilizing an overnight sleep test referred to as a polysomnogram. This is generally performed in a sleep lab and involves the continuous and simultaneous measurement and recording of an encephalogram, electromyogram, extraoculogram, chest wall plethysmogram, electrocardiogram, measurements of nasal and oral airflow, and pulse oximetry. All or some of these and other channels may be measured simultaneously throughout the night, and complex recordings of such measurement may then analyzed by a highly trained clinician to determine the presence or absence of sleep apnea.

BRIEF DESCRIPTION OF THE DRAWINGS

Advantages of the disclosure may become apparent upon reading the following detailed description and upon reference to the drawings in which.

DETAILED DESCRIPTION

Figure 1:
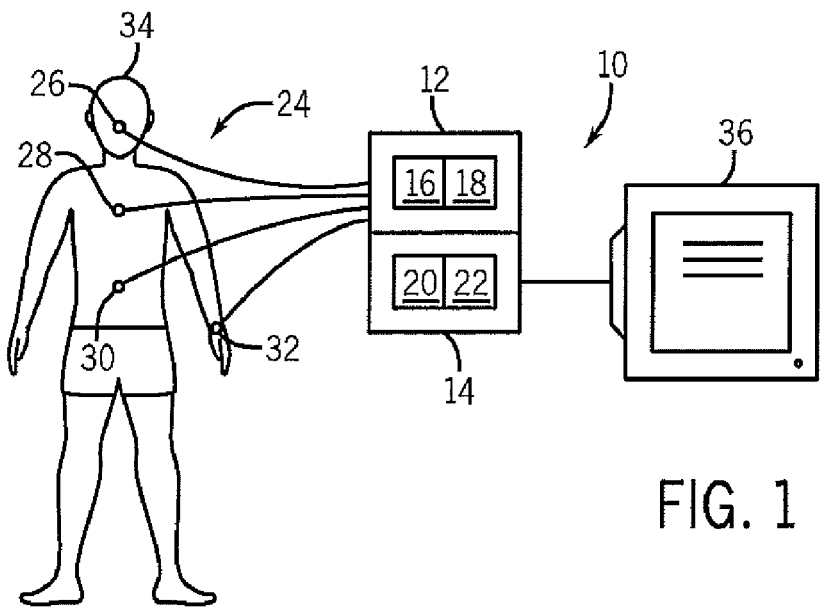
FIG. 1 is a block diagram of a medical analysis system in accordance with some embodiments.

One or more embodiments of the present disclosure will be described below. In an effort to provide a concise description of the embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Some embodiments are directed to automated systems and methods for detecting events that may be associated with sleep apnea. Specifically, some embodiments are directed to a system and/or method for automated detection of reduction in airflow events using polysomnograph (PSG) signals, wherein the reduction in airflow events may relate to sleep apnea. The PSG signals may be limited to four signals, including data from an airflow channel, a blood oxygen saturation ($SpO_2$) channel, a chest movement channel, and an abdomen movement channel. Using information from these channels, some embodiments may automatically identify reduction in airflow events.

Accordingly, some embodiments may facilitate automated detection and/or diagnosis of sleep apnea in patients. For example, some embodiments may be utilized to analyze data that has been acquired using a separate PSG system to determine whether sleep apnea related events have occurred. In another example, some embodiments may be incorporated with a PSG system to automatically detect and/or diagnose sleep apnea while a patient is being monitored. Indeed, some embodiments may facilitate detection of events relating to sleep apnea and/or facilitate diagnosis of sleep apnea in real time. Further, some embodiments may be utilized to demonstrate or confirm the accuracy or reliability of other systems and/or methods for detecting events related to sleep apnea. For example, some embodiments may be utilized in conjunction with a device configured to identify ventilatory instability (e.g., sleep apnea) based on an $SpO_2$ pattern recognition algorithm.

In some embodiments, a distinction may be made between whether identified sleep apnea events correspond to central sleep apnea or obstructive sleep apnea. Central and obstructive sleep apnea may be distinguished based on the nature of their occurrence. For example, a lack of effort in breathing is generally the cause of interrupted breathing associated with central sleep apnea, while a physical block in airflow despite effort is generally the cause of interrupted breathing associated with obstructive sleep apnea. If a patient is or is not making an effort to breathe, the patient's chest and abdomen activity may be indicative. Accordingly, some embodiments may distinguish between the two types of apnea by including devices or modules that are capable of quantifying phase differences between chest and abdomen signals. For example, some embodiments may include an algorithm stored on a memory that receives chest and abdomen signals and determines that certain events correspond to obstructive sleep apnea when the chest and abdomen signals are out of phase, or that the events correspond to central sleep apnea when there is no chest and/or abdomen movement, or there is a decrease in chest and abdomen movement but signals are in phase.

FIG. 1 is a block diagram of a medical analysis system in accordance with some embodiments. The medical analysis system is generally indicated by reference numeral 10. The system 10 includes a PSG system 12 and an event detection (ED) system 14. The PSG system 12 and the ED system 14 may be separate or integrated in accordance with some embodiments. The PSG system 12 may include, for example, hardware and/or software products from Nellcor Puritan Bennett's Sandman® sleep diagnostics line of products.

According to an embodiment, the PSG system 12 may include a memory 16 and a processor 18, and the ED system 14 may include a memory 20 and a processor 22. Programming stored on the respective memories 16 and 20 for the PSG system 12 and the ED system 14 may be utilized in conjunction with each system's respective processor 18 and 22 to facilitate performance of certain functions by the PSG system 12 and the ED system 14. For example, the memories 16 and 20 may include coded instructions that may be utilized with the respective processors 18 and 22 to perform automated methods in accordance with some embodiments. It should be noted that, in some embodiments, the memories 16 and 20 may be integral with the respective processors 18 and 22. Further, if the PSG system 12 and ED system 14 are integral components of the system 10, the integrated PSG system 12 and ED system 14 may share a single memory and/or a single processor.

According to an embodiment, the PSG system 12 may be capable of receiving signals from various sensors 24 that are capable of measuring certain physiologic parameters or patient activities. Specifically, the sensors 24 may include an airflow sensor 26, a chest sensor 28, an abdomen sensor 30, and a pulse oximeter sensor 32. Each of the sensors 24 may be attached to a patient 34 to facilitate measuring physiologic parameters and/or physical activity (e.g., movement) of the patient 34. These four measured values from the sensors 24 may be transmitted as signals to the PSG system 12 for processing. Thus, the sensors 24 may cooperate with the PSG system 12 to provide a polysomnogram. A polysomnogram may be described as a recording of an individual's sleep characteristics (e.g., activities and physiological events occurring during sleep), which may include an output of various measurements obtained by the sensors 24. Such an output may be recorded oil a memory (e.g., a flash memory or hard drive), presented on other tangible medium (e.g., printed on paper), or visually displayed (e.g., displayed as video). For example, the polysomnogram, along with other data, may be displayed on a video screen 36 of the medical analysis system 10.

According to an embodiment, the ED system 14 may be capable of using data acquired by the PSG system 12, such as the polysomnogram, to automatically detect events that may be associated with sleep apnea. For example, the ED system 14 may automatically detect reduction in airflow events, which relate to sleep apnea, using four PSG signals from the PSG system 12. The PSG signals may be transferred to the ED system 14 from the PSG system 14 in a number of ways. For example, data corresponding to signals from the PSG system 12 may be manually entered into the ED system 14, transferred via a memory device (e.g., a flash memory), or directly transmitted to the ED system 14 from the PSG system 12 for analysis. The PSG system 12 and the ED system 14 may receive and/or transmit signals corresponding to particular signal types based on data in a memory (e.g., a flash memory or a memory of the PSG system 12) and/or directly from each of the sensors 24. The PSG signals and/or signal data may be referred to as channels corresponding to each signal, such as airflow, chest, abdomen, and pulse oximetry channels.

According to an embodiment, once the ED system 14 receives the PSG signals, which may be in the form of signal data, the ED system 14 may perform an automated process on the PSG signals to identify events related to sleep apnea, such as reduction in airflow events. If certain events are identified in accordance with specified rules or criteria, the ED system 14 may provide an indication of the presence of ventilatory instability. For example, the ED system 14 may include hardware and/or software components that filter one or more of the PSG signals and identify characteristics of the signals that combine to suggest the presence of events related to sleep apnea. Specifically, for example, after checking for invalid data, filtered and unfiltered PSG signals may be utilized by the ED system 14 to estimate a value of breathes per minute (BPM) of the patient 34. The estimated BPM may then be utilized by the ED system 14 to calculate a baseline for use in determining whether a threshold level of airflow reduction is present. Further, the ED system 14 may determine whether certain other events indicative of respiratory instability are present based on the PSG signals, as will be discussed in further detail below. The ED system 14 may output values indicative of whether respiratory instability is present based on whether certain events were identified. For example, the ED system 14 may indicate the presence of sleep apnea and/or indicate a type of sleep apnea (e.g., central or obstructive) based on results obtained through analysis of a neural network of the ED system 14. It should be noted that the identification of events by the ED system 14 may be facilitated by an algorithm stored in the memory 20, which may cooperate with the processor 22 to implement methods in accordance with some embodiments. It should further be noted that the algorithm may be tuned by adjusting constant values in the algorithm to correspond to particular situations or patients (e.g., a patient with a heart condition).

Figure 2:
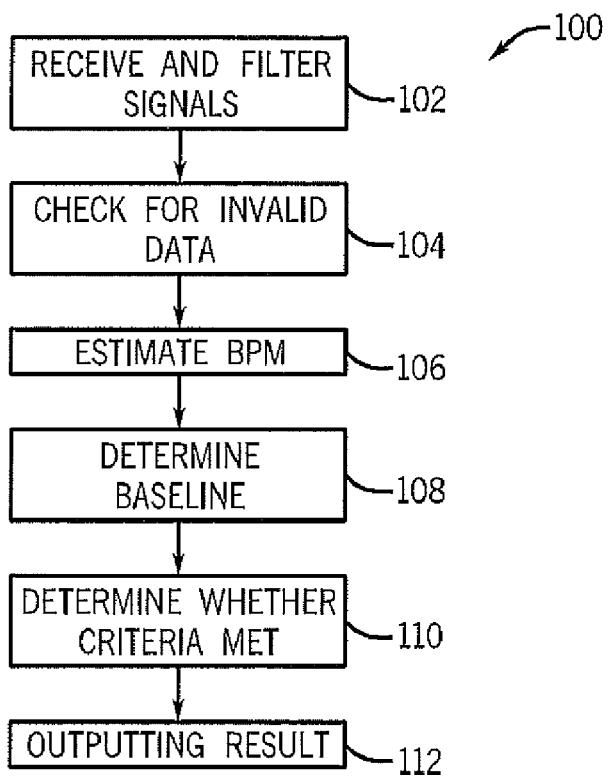
FIG. 2 is a process flow diagram of a method for detecting ventilatory instability related events in accordance with some embodiments.

FIG. 2 is a process flow diagram illustrating a method in accordance with some embodiments. The method is generally indicated by reference number 100 and includes various steps or actions represented by blocks. It should be noted that the method 100 may be performed as an automated procedure by a system, such as the analysis system 10. Further, certain steps or portions of the method may be performed by separate devices. For example, a first portion of the method 100 may be performed by the PSG system 12 and a second portion of the method 100 may be performed by the ED system 14. In this embodiment, the method includes receiving and filtering signals (block 102), checking for invalid data (block 104), estimating BPM (block 106), determining a signal baseline for certain signals (block 108), determining whether certain criteria are met by acquired data (block 110), and outputting a result (block 112).

According to an embodiment, the method 100 begins with receiving and filtering signals, which may include signal data, as represented by block 102. Block 102 may include receiving and/or filtering signal data from several sensors, which may include the airflow sensor 26, the chest sensor 28, the abdomen sensor 30, and/or the pulse oximeter sensor 32.

Figure 3:
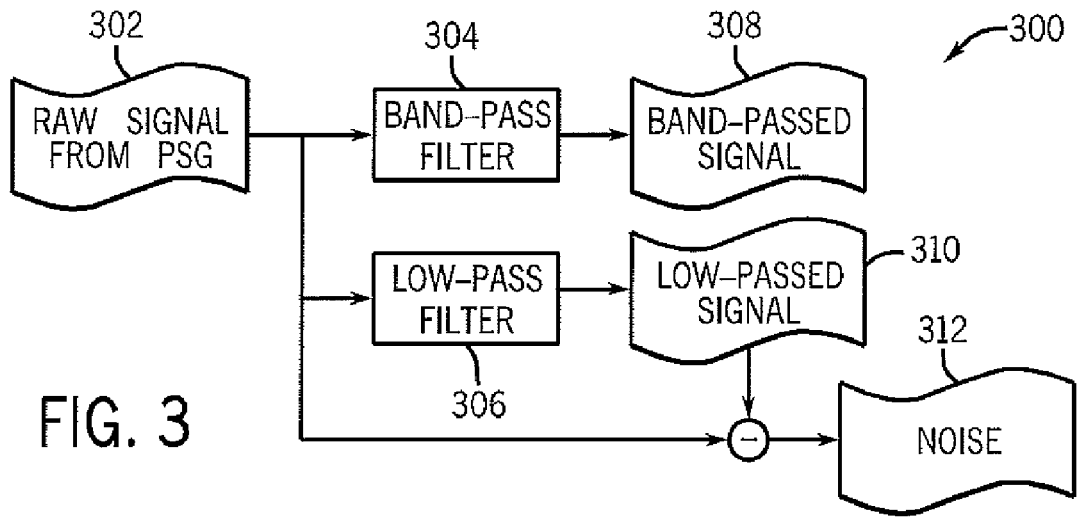
FIG. 3 is a block diagram of a device and/or module capable of receiving and filtering signals in accordance with some embodiments.

Specifically, block 102 may represent receiving data or signals from airflow, chest, abdomen, and pulse oximetry channels and filtering signals on a subset of the channels. Signals on the chest, airflow, and abdomen channels may be filtered, while signals on the pulse oximetry channel, which may relate to $SpO_2$ data, may remain unfiltered. For example, FIG. 3 illustrates a component 300 capable of filtering the chest, airflow, and abdomen channels in accordance with some embodiments. In some embodiments, the component 300 may be a feature of the processor, or it may be implemented using electronic circuits which preprocess and filter some or all of the PSG signals. 22. Specifically, as illustrated in FIG. 3, a raw signal 302 from the PSG system 12, such as a signal on the chest, airflow or abdomen channel, may be received into the component 300 of the ED system 114. The raw signal 302 may pass through the component 300, which may include passing the raw signal through a band-pass filter 304 and a low-pass filter 366 of the component 300.

According to an embodiment, the band-pass filter 304 may pass frequencies within a selected range and attenuate frequencies that are outside of the selected range. Specifically, for example, the band-pass filter 30 may include a 0.0833-1 Hz band-pass filter that operates to pass frequencies corresponding to 5-60 BPM and filter out frequencies above and below that range. An initial or default 5-60 BPM pass band may be used since most human breathing rates will be within this range under typical sleep-lab conditions. The pass band may be tuned (moved, narrowed, and/or widened) by the operator based on known patient conditions to increase the specificity and/or sensitivity of the ED system. Once the raw signal 302 has passed through the band-pass filter 304, it becomes a band-passed signal 308. The band-passed signal 308 may be utilized in conjunction with other input in the analysis and identification of ventilatory instability, as will be discussed in further detail below.

According to an embodiment, the low-pass filter 306 may pass frequencies below a cutoff level and attenuate frequencies higher than the cutoff level. Specifically, for example, the low-pass filter 306 may attenuate frequencies lower than 0.04166 Hz, which corresponds to 2.5 BPM. 2.5 BPM may be selected as the initial cutoff level since it is unlikely that any patient will breathe slower than this rate, and therefore frequencies below this level can be considered noise, or more specifically these frequencies can be considered the DC offset of the PSG signal. The operator may move the low-pass filter level based on known patient conditions in an attempt to increase the specificity and sensitivity of the ED system. Once the raw signal 302 has passed through the low-pass filter 306, it becomes a low-passed signal 310. The low-passed signal 310 may be used to calculate a noise signal 312 by passing it through a subtraction block 314 with the raw signal 302 to get a difference between the raw signal 302 and the low-passed signal 310. This and other features of noise calculation will be discussed in further detail below. The calculated noise level may be utilized to clarify signal features by reducing noise content. In some embodiments, features may be included that facilitate reading data through the noise, rather than merely removing the noise.

According to an embodiment, after the signals have been received and/or filtered in block 102, the method 100 may proceed to block 104, which includes checking for invalid data. Specifically, block 104 may represent receiving and processing a stream of data to determine whether any portions of the data meet criteria indicating that the data should be discarded. For example, block 104 may represent receiving a 10 minute segment of data that is analyzed to determine if the following criteria are present: (1) the $SpO_2$ signal is less than a designated value (e.g., less than a value of 20% $SpO_2$, which may indicate that the sensor is off or disconnected), (2) the signal to noise ratio for a signal on the airflow channel is less than a designated value (e.g., 5 dB), (3) the signal to noise ratio for a signal on the chest channel is less than a designated value (e.g., 0 dB), and/or (4) a signal to noise ratio (SNR) for a signal on the abdomen channel is less than a designated value (e.g., 0 dB). If it is determined in block 104 that any of the designated criteria, such as the criteria set forth above, are present for a designated period, e.g., 2 minutes, within the 10 minute segment of data, all or part of the 10 minute segment of data may be discarded as being invalid. In some embodiments, features may be included that facilitate reading through data with a SNR below a threshold, rather than merely invalidating data because of low SNR values.

It should be noted that the signal to noise ratios referenced above may be automatically calculated in block 104 along with other determinations relating to identifying invalid data. For example, block 104 may represent calculating the signal to noise ratio for a particular signal by first removing DC from the raw signal 302. That is, the low-passed signal 310 (LPFilteredSignal) may be subtracted from the raw signal 302 (RawSignal) to obtain a raw signal without DC (RawSignalNoDC). This procedure may be represented by the following equation:

$$RawSignalNoDC=RawSignal-LPFilteredSignal.$$

Noise may then be calculated by subtracting the band-passed signal 308 (BPSignal) from the raw signal without DC. This procedure may be represented by the following equation:

$$Noise=RawSignalNoDC-BPSignal.$$

A statistical measure of magnitude, such as a root mean square, may then be obtained for both the noise and the band-passed signal, and the signal to noise ratio (SNR) may be calculated by dividing the root mean square of the band-passed signal (RMS(Signal)) by the root mean square of the noise (RMS(Noise)), as represented by the following equation:

$$SNR=RMS(Signal)/RMS(Noise).$$

As will be appreciated, in some embodiments, different calculations or procedures may be utilized to obtain the signal to noise ratio.

Figure 4:
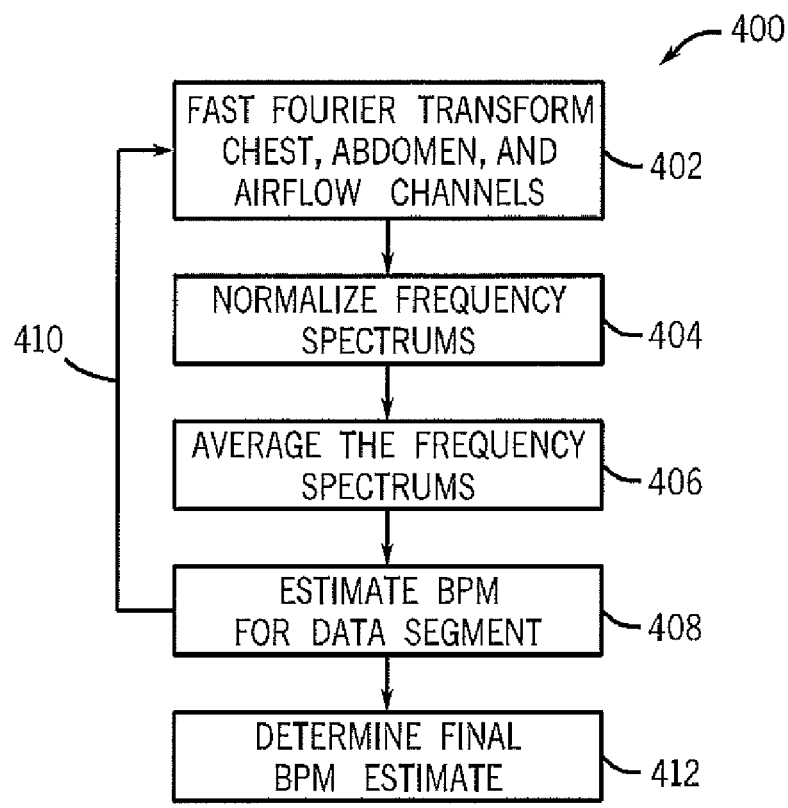
FIG. 4 is a process flow diagram of a method for estimating a value for breathes per minute of a patient in accordance with some embodiments.

According to an embodiment, after invalid data has been removed in block 104, the method 100 may proceed to determine an estimated BPM based on the received data, as represented by block 106. As illustrated in FIG. 4, the BPM estimate may be calculated using the chest, abdomen, and airflow signals. FIG. 4 is a process flow diagram of a method of estimating BPM in accordance with some embodiments. The method of estimating BPM is generally indicated by reference number 400 and includes various steps or actions represented by blocks. As with the other steps of the method 100, the method 400 may be performed as an automated procedure by the system 100 in accordance with some embodiments.

According to an embodiment, the method 400 begins by receiving band-passed airflow, chest, and abdomen signals, and converting the signals to the frequency domain by performing a fast Fourier transform (FFT) on all three channels, as represented by block 402. Specifically, block 402 may represent determining an FFT for the three channels a certain number of times per time period. For example, block 402 may represent calculating an FFT for the band-passed airflow, chest, and abdomen signals once every 2 minutes.

According to an embodiment, after performing the frequency conversion in block 402, the method 400 may proceed to block 404, which represents normalizing the frequency spectrums obtained in block 402. The procedure represented by block 404 may include various different types of normalization, which may result in ranging the frequency spectrums from 0.0 to 1.0. For example, peak normalization may be performed by dividing the amplitude at each point in the spectrum of each signal by the maximum amplitude of that particular spectrum. Thus, the normalized spectrum may include intensities that range from as low as 0.0 to as high as 1.0. By normalizing the spectrums, certain discrepancies between the spectrums may be removed to facilitate proper combination or comparison of the different spectrums. It should be noted that each spectrum may be based on a segment of data, such as a 10 minute segment of recorded sensor data.

According to an embodiment, after the spectrums have been normalized in block 404, all three frequency spectrums may be averaged, as represented by block 406, and an estimate of BPM may be calculated based on the average, as represented by block 408. Specifically, blocks 406 and 408 may include averaging all of the histograms of the frequency spectrums and selecting a frequency from the average that has the highest amount of energy to determine the estimate BPM for the associated segment of data. This procedure may be represented by the following equation:

$$\text{BPM Estimate} = \max(\text{Average Frequency Spectrum}).$$

According to an embodiment, the process of providing BPM estimates for a segment of data may be repeated for a series of data segments, as represented by arrow 410. The most recent BPM estimate obtained for a data segment may be referred to as the current estimate and the penultimate BPM estimate obtained for a previous data segment may be referred to as the previous estimate. In other words, once a new segment of data has been received and processed, the BPM estimate that was the current estimate may become the previous segment and the BPM estimate for the most recent segment of data may become the current estimate. As represented by block 412, the current and previous estimates may be averaged to provide a final BPM estimate, as represented by the following equation:

$$\text{Final BPM Estimate} = 0.5(\text{Current Estimate} + \text{Previous Estimate}).$$

It should be noted that in some embodiments, more than two estimates may be averaged to determine the final BPM estimate. For example, three or more estimates for a series of data segments may be stored and averaged to determine a final BPM estimate in accordance with some embodiments.

According to an embodiment, after estimating BPM in block 106, the method 100 may proceed to determining a signal baseline for each signal, as represented by block 108. Specifically, for example, block 108 may include calculating a signal baseline for the airflow, chest, and abdomen signals. In performing this calculation, a root mean square value for the signal (e.g., the raw signal 302) may first be obtained using the final BPM estimate and a running root mean square, as indicated by the following equation:

$$X_{rms} = 0.5 \text{ BPM running RMS signal } X.$$

This calculation may take into account every point of a signal such that the results are indicative of the power of the signal at each point. The baseline value (X-Baseline) for each particular signal may then be determined based on this root mean square value ($X_{rms}$). Specifically, the baseline may be determined as the top 10% or ninetieth percentile of the root mean square value, as represented by the following equation:

$$X\text{-Baseline} = \text{Top } 10\% \text{ (90th percentile) of } X_{rms}.$$

According to an embodiment, once a baseline has been determined for the airflow, chest, and abdomen signals, as represented by block 108, the method 100 may proceed with determining whether certain criteria are met, as represented by block 110. The presence of characteristics that meet certain criteria may indicate and confirm that a reduction in airflow (RAF) event occurred relative to a normal airflow. For example, a determination may be made as to whether a certain level of reduction (e.g., a 40% reduction) in airflow has occurred for at least a threshold amount of time (e.g., 10 seconds). This may be referred to as an RAF event. Specifically, in one embodiment, an RAF event may be described as an interval where the amplitude envelope of a signal on the airflow channel from the PSG system 12 is reduced at least 40% relative to the baseline for at least 10 seconds consecutively. It should be noted that the amplitude envelope may refer to the value of a function describing how the maximum amplitude of the airflow signal changes over time.

According to an embodiment, once an RAF event has been identified, it may be qualified for consideration based on certain scoring rules. For example, an RAF event may be disqualified if there is not a specified amount of change in one or more other signal measurements within a certain window of time with respect to the time the RAF event occurred. For example, if the measured $SpO_2$ value does not change at least a certain amount, e.g., 3%, during the RAF event or within a certain time, e.g., 30 seconds, after the RAF event, the RAF event may be disqualified. Similarly, for example, if there is not at least a certain change, e.g., a 40% reduction, in the chest or abdomen signal from the PSG system 12 for at least part, e.g., half, of the interval of the RAF event, the RAF event may be disqualified. Alternatively, if the available data meets these criteria, the RAF event may be qualified and used to determine whether the data is indicative of ventilatory instability in the patient that was or is being monitored.

According to an embodiment, block 110 may also represent determining whether a segment of data includes an indication of ventilatory instability based on a quantity of qualified RAF events that occur within the data segment. For example, block 110 may determine that a particular data segment is indicative of ventilatory instability if a certain number, e.g., at least 5, of consecutive RAF events are qualified within a given portion, e.g., a 10 minute period, of the segment of data. Thus, segments of data may be divided into intervals, e.g., 10 minute intervals, in accordance with some embodiments. It should be noted that in order for the RAF events to be qualified as being consecutive, certain relative timing criteria may have to be met. For example, in one embodiment, for a pair of qualified RAF events to be consecutive, the RAF events must occur within a certain time, e.g., 120 seconds, of one another.

According to an embodiment, block 110 may also represent determining a type of respiratory event, such as determining the presence of central or obstructive sleep apnea based on correlations between different signals, such as the chest and abdomen signals being in or out of phase. As discussed above, central and obstructive sleep apnea may be distinguished based on the nature of their occurrence. For example, a lack of effort in breathing is generally associated with central sleep apnea, while a physical block in airflow despite effort is generally associated with obstructive sleep apnea. A patient's chest and abdomen activity may be utilized to distinguish between the two types of apnea. Accordingly, some embodiments may include features that are capable of quantifying phase differences between chest and abdomen signals. For example, some embodiments may include features that determine that certain events correspond to obstructive sleep apnea when the chest and abdomen signals are out of phase, or that the events correspond to central sleep apnea when there is no chest and/or abdomen movement, or there is a decrease in chest and abdomen movement but signals are in phase.

Based on the criteria or rules discussed above, the method 100 may output an epoch score for each data segment, as represented by block 112. For example, an epoch score may be repeated once every time a segment of data has been analyzed (e.g., once every 10 minutes). In some embodiments, a system may utilize such a score in an algorithm to provide an indication of certain conditions relating to ventilatory instability. For example, the epoch score may include a value of 1 for an indication that sleep apnea has been detected, 0 for an indication that sleep apnea has not been detected, or −1 for an indication of invalid data. The indicator provided by the system based on the score may include a textual indication of the detected condition, such as "sleep apnea detected," "sleep apnea not detected", or "unknown or invalid data." In some embodiments, a series of epoch scores may be combined for all or part of a sleep study to generate an aggregate score. For example, an average of all of the scores for each 10 minute segment of a sleep cycle may be used to determine a summary score for a particular patient.

Further, in some embodiments, the severity of the ventilatory instability or apnea events may be quantified instead of merely providing binary outputs. For example, the depth of the airflow reduction may be used to quantify a severity of the ventilatory instability. In some embodiments different aspects associated with qualified RAF events may be used to determine levels of severity. For example, a series of continually larger drops in airflow and/or continual failures to return to a baseline level of airflow may be correlated to a higher level of severity. Further, numerous clusters of RAF events or data segments including RAF events may be considered in determining a severity level. For example, a large segment of data, e.g., 4 hours of data, may include various sub-segments having different levels of apnea. Each sub-segment may be analyzed separately based on certain criteria, such as a number of RAF events per time period, an amount of reduced airflow, or other characteristics, and the values associated with the sub-segments may be combined to provide an overall ventilatory instability level for the large segment of data.

Figure 5:
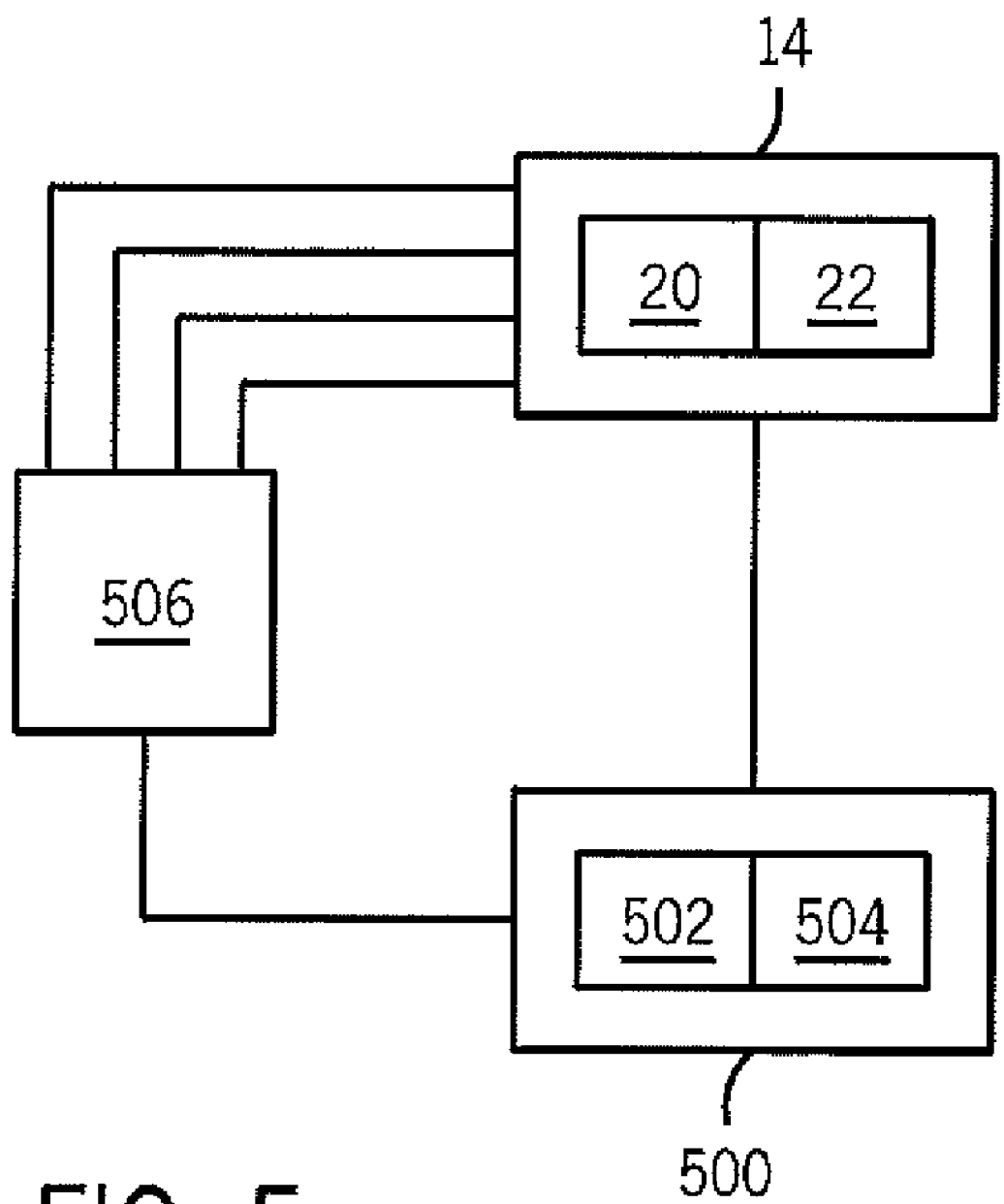
FIG. 5 is a block diagram of the system of FIG. 1 communicatively coupled with a separate ventilatory instability detection system to facilitate calibration of the separate system in accordance with some embodiments.

The ED system 14 may be utilized to demonstrate or confirm that other systems involving detection of ventilatory instability related events are properly calibrated and/or providing results that correlate to the results obtained by the ED system 14. For example, FIG. 5 is a block diagram of the ED system 14 communicatively coupled with a separate ventilation analysis system 500 to facilitate calibration of the system 500 or to confirm its proper operation. The separate ventilation analysis system 500 may include a system such as that described in U.S. Pat. No. 6,223,064. For example, the system 500 may include an SpO$_2$ pattern recognition system that is utilized to identify ventilatory instability based on a series of SpO$_2$ values. The system 500 may include a memory 502 and a processor 504 that are capable of analyzing input received or previously acquired from a single SpO$_2$ sensor. Specifically, the system 500 may be capable of identifying certain patterns or clusters of measured SpO$_2$ values to identify events related to ventilatory instability.

According to an embodiment, the ED system 14 may facilitate adjustment and/or calibration of the system 500 to correlate with BPM estimates determined by the ED system 14. For example, both systems 14 and 500 may be provided with data from a storage device 506, wherein the data corresponds to certain ventilatory instability events that have been observed. During a calibration period, the system 500 may be adjusted to correspond to the ED system 14. In other words, the system 500 may be adjusted such that it detects a high percentage of the ventilatory instability events detected by the ED system 14. For example, certain coefficients of an algorithm stored on the memory of the system 500 may be adjusted to improve correlations between the results for the system 500 and the results for the ED system 14.

In a specific example, the ED system 14 may utilize automated analysis of the data obtained via the various sensors 24 to confirm that the system 500 is properly tuned and/or providing corresponding output. Specifically, the ED system 14 may receive data from the storage device 506 corresponding to airflow, chest impendence, abdomen impedance, and blood oxygen saturation, and use this data to provide results that include a BPM estimate. These results may be compared with similar results obtained by the system 500 using SpO$_2$ pattern recognition. Based on the comparison, certain features of the system 500 (e.g., features of a pattern recognition algorithm stored on the memory 502) may be adjusted to achieve a desired correspondence. The automated analysis provided by the ED system 14 may facilitate rapid adjustment and/or testing of systems such as the system 500.

Specific embodiments have been shown by way of example in the drawings and have been described in detail herein. However, it should be understood that the claims are not intended to be limited to the particular forms disclosed. Rather, the claims are to cover all modifications, equivalents, and alternatives failing within their spirit and scope.

What is claimed is:

1. A system, comprising:
    a processing device configured to:
        calculate an output value of breathes per minute for a data segment based on signals of an airflow channel, a chest channel, and/or an abdomen channel and/or combinations thereof;
        calculate a baseline value for each of the airflow channel, the chest channel, and the abdomen channel based at least in part upon the output value of breathes per minute and a measure of the magnitude of the corresponding signal;
        determine whether a reduction in airflow above a minimum reduction level relative to the baseline value for the airflow channel has been maintained for a period of time and identify a reduction in airflow event if the reduction in airflow is above the minimum reduction level;
        determine if the reduction in airflow event is qualified by determining whether a specified amount of change has occurred in the chest channel or the abdomen channel during a window of time including the reduction in airflow event; and
        provide an indication of ventilatory instability if the reduction in airflow event is identified and qualified.

2. The system of claim 1, comprising a filter capable of filtering the airflow channel, the chest channel, and/or the abdomen channel.

3. The system of claim 2, comprising a filter capable of band-pass filtering and low-pass filtering the airflow channel, the chest channel, and the abdomen channel, while passing the pulse oximetry channel.

4. The system of claim 1, comprising a monitor capable of displaying the indication of ventilatory instability.

5. The system of claim 1, wherein the processing device is configured to determine whether the indication of ventilatory instability corresponds to central sleep apnea or obstructive sleep apnea based on signals of the chest channel and abdomen channel being in a phase or out of phase.

6. The system of claim 1, comprising an integral polysomnograph system capable of providing the signals of the airflow channel, the chest channel, and the abdomen channel.

7. The system of claim 1, comprising a pulse oximetry sensor; an airflow sensor, a chest sensor, and an abdomen sensor.

8. A system, comprising:
a polysomnograph system capable of supplying signals of an airflow channel, a chest channel, an abdomen channel, and a pulse oximetry channel;
an event detection system including a processing device configured to:
calculate a baseline value for each of the airflow channel, the chest channel, and the abdomen channel based at least in part upon a value of breathes per minute and a measure of the magnitude of the corresponding signal;
identify a reduction in airflow event when a reduction in airflow above a minimum reduction level relative to the baseline value for the airflow channel has been maintained for a threshold period of time; and
determine if the reduction in airflow event is qualified by determining whether a specified amount of change has occurred in the chest channel, the abdomen channel, or the pulse oximetry channel during a window of time including the reduction in airflow event; and
a pulse oximetry pattern recognition system capable of identifying ventilatory instability based at least in part upon a series of blood oxygen saturation values; and
a system calibration component capable of comparing results from the event detection system and the pulse oximetry pattern recognition system to facilitate adjustment of the pulse oximetry pattern recognition system.

9. The system of claim 8, wherein the processing device of the event detection system is configured to calculate the value of breathes per minute for a data segment based on signals of the airflow channel, the chest channel, and/or the abdomen channel and/or combinations thereof.

10. The system of claim 9, wherein the processing device of the event detection system is configured to calculate the value of breathes per minute by averaging an estimate of breathes per minute for each of a plurality of data segments based at least in part upon the signals of the airflow channel, the chest channel, and/or the abdomen channel and/or combinations thereof.

11. The system of claim 9, comprising a display, wherein the event detection system is configured to provide an indication of ventilatory instability on the display if the reduction in airflow event is identified and qualified.

12. The system of claim 8, wherein the processing device of the event detection system is configured to convert the signals of the airflow channel, the chest channel, and/or the abdomen channel to a frequency domain, and wherein the event detection system is configured to determine a plurality of frequency spectrums, wherein the plurality of frequency spectrums comprises an airflow channel frequency spectrum, a chest channel frequency spectrum, and/or an abdomen channel frequency spectrum.

13. The system of claim 12, wherein the processing device of the event detection system is configured to calculate the value of breathes per minute for a data segment based on determining a highest frequency of respective averages of the plurality of frequency spectrums.

14. The system of claim 8 wherein the system calibration component is capable of adjusting features of the pulse oximetry pattern recognition system to achieve a desired correspondence between respective results of the pulse oximetry pattern recognition system and the event detection system.

* * * * *